(12) United States Patent
Zuber et al.

(10) Patent No.: US 8,945,927 B2
(45) Date of Patent: Feb. 3, 2015

(54) POLYMERS FOR DELIVERING MOLECULES OF INTEREST

(75) Inventors: Guy Zuber, Illkirch (FR); Benoit Frisch, Strasbourg (FR); Gaelle Creusat, Fleville Devant Nancy (FR); Jean-Sebastien Thomann, Culin (FR)

(73) Assignees: Universite de Strasbourg, Strasbourg (FR); Centre National de la Recherche Scientifique, Paris Cedex (FR)

( * ) Notice: Subject to any disclaimer, the term of this patent is extended or adjusted under 35 U.S.C. 154(b) by 23 days.

(21) Appl. No.: 13/637,412

(22) PCT Filed: Mar. 29, 2011

(86) PCT No.: PCT/EP2011/054795
§ 371 (c)(1),
(2), (4) Date: Dec. 4, 2012

(87) PCT Pub. No.: WO2011/120953
PCT Pub. Date: Oct. 6, 2011

(65) Prior Publication Data
US 2013/0096177 A1    Apr. 18, 2013

Related U.S. Application Data

(60) Provisional application No. 61/318,598, filed on Mar. 29, 2010.

(51) Int. Cl.
| | |
|---|---|
| *C12N 15/87* | (2006.01) |
| *A61K 9/00* | (2006.01) |
| *C08G 69/48* | (2006.01) |
| *A61K 47/34* | (2006.01) |
| *C08G 73/02* | (2006.01) |
| *C08L 79/02* | (2006.01) |

(52) U.S. Cl.
CPC ............ *A61K 47/34* (2013.01); *C08G 73/0206* (2013.01); *C08L 79/02* (2013.01); *C12N 15/87* (2013.01)
USPC ........ 435/463; 435/455; 435/458; 424/78.18; 424/78.19; 424/486; 528/332

(58) Field of Classification Search
None
See application file for complete search history.

(56) References Cited

PUBLICATIONS

Database CAPLUS on STN, Acc. No. 1963:14571, Schickh, DE 1135450 (Aug. 30, 1962) (abstract).*
Creusat, G. et al. "Self-Assembling Polyethylenimine Derivatives Mediate Efficient siRNA Delivery in Mammalian Cells" *ChemBioChem*, Nov. 1, 2008, pp. 2787-2789, vol. 9, No. 17, XP-002525420.
Zaghloul, E. M. et al. "Formulation and Delivery of Splice-Correction Antisense Oligonucleotides by Amino Acid Modified Polyethylenimine" *Molecular Pharmaceuticals*, Feb. 3, 2010, pp. 652-663, vol. 7, No. 3, XP-002644387.
Written Opinion in International Application No. PCT/EP2011/054795/, Jul. 8, 2011, pp. 1-6.

* cited by examiner

*Primary Examiner* — Brian J Davis
(74) *Attorney, Agent, or Firm* — Saliwanchik, Lloyd & Eisenschenk

(57) ABSTRACT

The present invention relates to a new class of cationic polymers that self-assemble with a pH-sensitive dissolution switch, and their uses to deliver molecules of interest to a cell. The present invention also relates to compositions comprising said cationic polymers non-covalently associated with a molecule of interest, in particular with a siRNA.

26 Claims, 14 Drawing Sheets

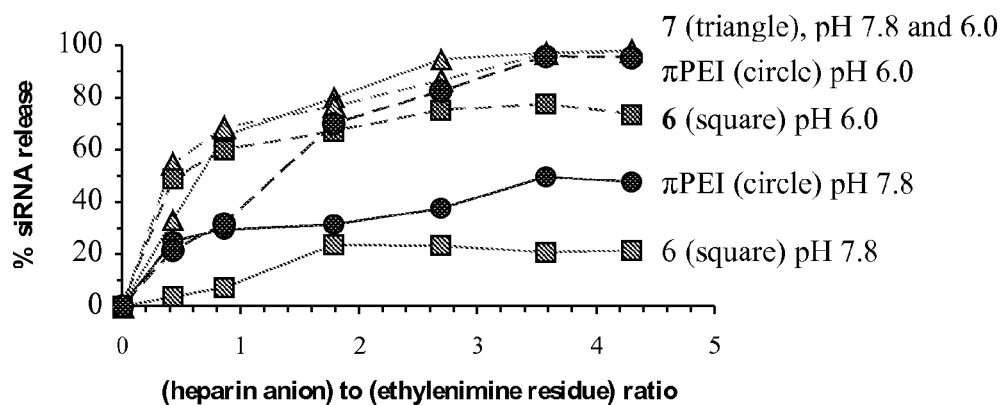
Figure 18
Fig. 19A
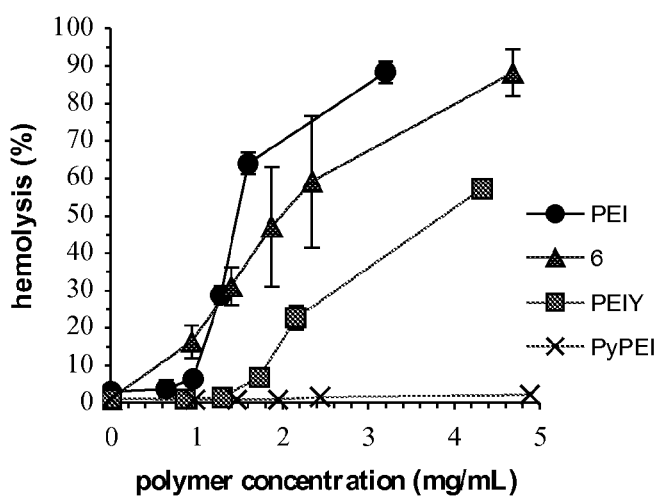
Fig. 19B
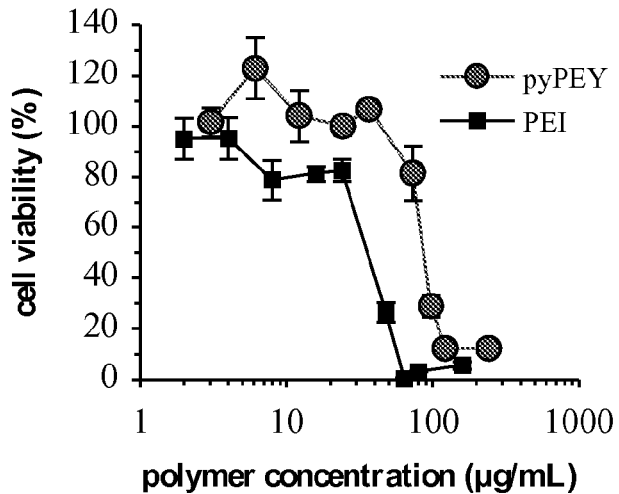

POLYMERS FOR DELIVERING MOLECULES OF INTEREST

CROSS-REFERENCE TO RELATED APPLICATIONS

This application is the U.S. national stage application of International Patent Application No. PCT/EP2011/054795, filed Mar. 29, 2011, which claims the benefit of U.S. Provisional Patent Application No. 61/318,598, filed Mar. 29, 2010.

The Sequence Listing for this application is labeled "SeqList.txt" which was created on Sep. 25, 2012 and is 2 KB. The entire contents of the sequence listing is incorporated herein by reference in its entirety.

FIELD OF THE INVENTION

The present invention relates to a new class of cationic polymers that are effective delivery agents for molecules of interest and that exhibit a toxicological profile with low toxicity or which is suitable for in vivo administration. In particular, the invention relates to means, composition and methods, to form highly effective delivery systems for synthetic oligonucleotides and nucleic acids that can interfere with biological and cellular mechanisms.

BACKGROUND OF THE INVENTION

RNA interference (RNAi) is a sequence-specific and post-transcriptional gene silencing process present in animals and plants and is mediated by 21-22 nt long RNA duplexes, called small interfering RNA (siRNA). This gene silencing mechanism appears to be particularly effective and holds great potential for decoding gene function and as gene-specific therapeutics. However, oligonucleotides do not diffuse freely across plasma membrane and imperiously depend on formulation within synthetic delivery systems.

RNA-splicing is a process by which a single pre-mRNA transcript can be alternatively spliced to produce multiple mRNA variants which in turn will be translated to different protein isoforms. In fact, up to 70% of human genes undergo alternative splicing and more importantly, up to 50% of human genetic diseases are known to arise from mutations that affect splicing. Moreover, aberrations in alternative splicing have been observed in many cancer-related genes. Therefore, optimization of drugs that can correct splicing mutations has recently become of great interest. Among ongoing splice correction trials, phosphorothioated oligonucleotides with 2'-O-methyl modifications are, particularly, found to be promising potential therapeutic agents for such diseases. Numerous studies have already reported on the therapeutic potential of splice-switching oligonucleotides by targeting several diseases caused by aberrant splicing such as Duchenne muscular dystrophy, β thalassemia and therosclerosis. While new generations of oligonucleotides are more resistant to degradation, their therapeutic use is still limited because of their poor pharmacological properties (Kurreck et al., 2003).

Non-viral delivery vehicles were initially developed for plasmid delivery (Felgner, 1999; Neu et al., 2005). They are generally cationic lipids or cationic polymers that interact electrostatically with the nucleic acid phosphate backbone to form stable complexes. These cationic complexes in turn bind to anionic proteoglycans present on cell surfaces, enter cells within membrane-coated vesicles and experience acidification on their road to degradative compartments. Escape from this pathway is required and relies on the incorporation of fusogenic lipids or endosomolytic functions within the complexes. Among the cationic polymers, polyethylenimine or PEI (patent application WO 96/02655) is certainly the most used plasmid DNA transfection agent because its high buffering capacity in the pH range between 5.0 and 7.5 facilitates rupture of endosomal membranes via a "proton sponge" mechanism. However, PEI, was shown to be a poor siRNA delivery agent (Grayson et al., 2006), especially in comparison to lipids.

Numerous approaches and hypotheses have been investigated to create efficient polymer-based delivery vehicles dedicated to siRNA. While siRNA duplexes and genes share a similar anionic charge density, the reduced number of anionic charges of a siRNA duplex in comparison to a plasmid DNA (average anionic charge of 7000) reduces the electrostatic cohesion of the soluble PEI with siRNA. Polyanionic proteoglycans present outside the cells and on the cell surfaces may then effectively displace PEI from the complexes, resulting in release of siRNA in the extracellular medium. No delivery and siRNA-mediated gene silencing can consequently occur.

Increased stability of oligonucleotide polyplexes may be performed by different means. siRNA duplexes could be artificially transformed into long structures, like plasmid DNA by equipment with self-complementary and overhanging nucleotides (Bolcato-Bellemin et al., 2007). Oligonucleotides could be conjugated with cholesterol for enhanced anchorage to cationic micelles (Zimmermann et al., 2006) or to cationic peptide so as to obtain an overall self-aggregating and cationic species (Fraley et al., 2006). Interestingly, it was shown that modification of PEI with natural amino-acids and in particular aromatic ones (patent application WO 2009/074970) led to a polymer with excellent siRNA delivery ability in eucaryotic cells. Use of aromatic alpha-aminoacids seemed particularly important since the amino-acid offers simultaneous possibilities to interact with the siRNA by electrostatic interactions (via the alpha-amine), hydrophobic and stacking interactions, leading to stable siRNA polyplexes.

However, nucleic acid translocation into the cell must involve a rupture of the lipid membrane integrity and some PEI conjugates may induce direct membrane destabilization. These polymers with membrane-perturbing activity at extracellular pH may exhibit hemolytic activity and lead to cell lethality. Thus, the use of cationic polymers, in particular PEI, often is limited by its cytotoxicity and so far has not been approved for use in humans.

To reduce the cytotoxicity of PEI, PEI has been modified, for example, with dextran sulfate, human serum albumin or polyethylene glycol, but all modified PEI show lower nucleic acid delivery efficiency than unmodified PEI.

Consequently, there is a strong need of developing cationic polymers that are efficient to deliver synthetic oligonucleotides and having a toxicological profile which is suitable for in vivo administration.

SUMMARY OF THE INVENTION

The present invention describes a new class of cationic polymers that self-assemble (either with or without oligonucleotides) with a pH-sensitive dissolution switch. Such property permits to stabilize the cohesion of the siRNA polyplexes in extracellular media (pH favoring self-aggregation of the polymer and oligonucleotide entrapping within the polymer self-aggregates) while still enabling release of the oligonucleotide into the cell via dissolution of the aggregates following cell internalization into acidic intracellular vesicles.

In a first aspect, the present invention concerns a cationic polymer, preferably a polyethylenimine, having multiple amine functions modified or substituted by a radical X, wherein X is C(=Z)—R$_1$ wherein Z is S or O; and R1 is selected from the group consisting of

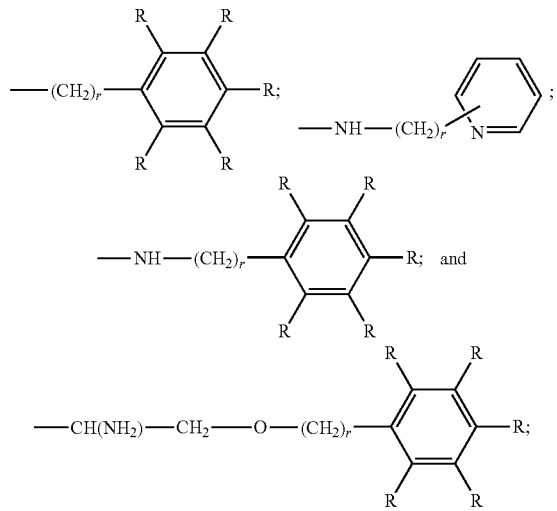

and optionally a combination thereof wherein r is an integer from 0 to 2, R are independently selected from the group consisting of H, OH, OCH$_3$, NH$_2$, O(CH$_2$CH$_2$O)$_m$H, and O(CH$_2$CH$_2$O)$_m$CH$_3$ with m being an integer between 1 and 500.

In an embodiment, the cationic polymer of the invention is branched.

In an embodiment, the cationic polymer of the invention has a molecular weight of at least 400 Da, preferably from 500 Da to 200,000 Da.

In an embodiment, the amine functions of the polymer of the invention are modified or substituted by a radical X at a ratio of p from 0.1 to 0.9, preferably from 0.15 to 0.5, more preferably from 0.2 to 0.4, still more preferably about 0.30.

In an embodiment, R is independently selected from the group consisting of H, OH, OCH$_3$, and NH$_2$.

In an embodiment, r may be r is 0 or 1.

In an embodiment, X is selected from the group consisting of

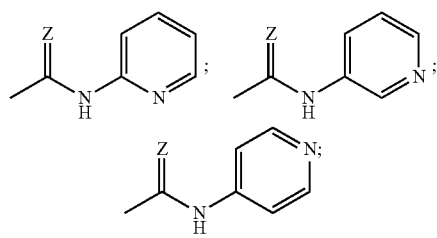

and optionally a combination thereof. Preferably, Z is S. Preferably, X is

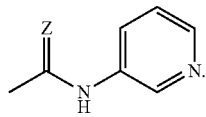

In an embodiment, X is selected from the group consisting of

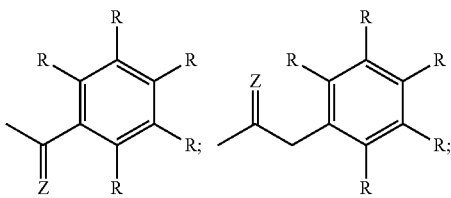

and optionally a combination thereof. Preferably, X is

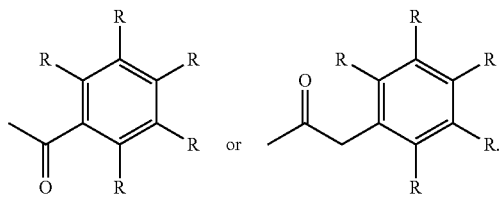

In an embodiment, at least 3 or 4 of the 5 R are H and the other R are selected from the group consisting of H, OH, NH$_2$, and OCH$_3$, more preferably of H, OH, and OCH$_3$.

In an embodiment, X is selected from the group consisting of

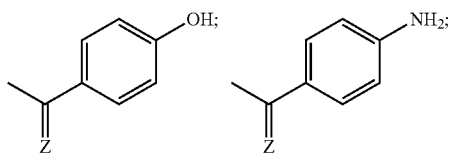

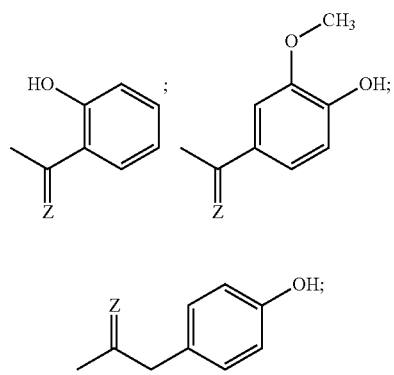

and optionally a combination thereof. Preferably, X is O.

In another embodiment, R1 is

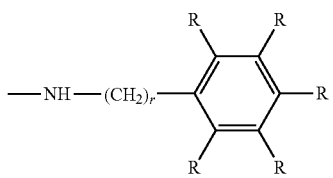

with 4 of the R being H and the other R being NH2, preferably in para. Preferably, Z is S and r is 0.

In another embodiment, X is C(=Z)—R1 and $R_1$ is

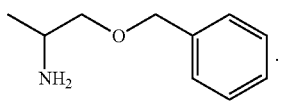

Preferably, Z is O.

In another embodiment, X is selected from the group consisting of

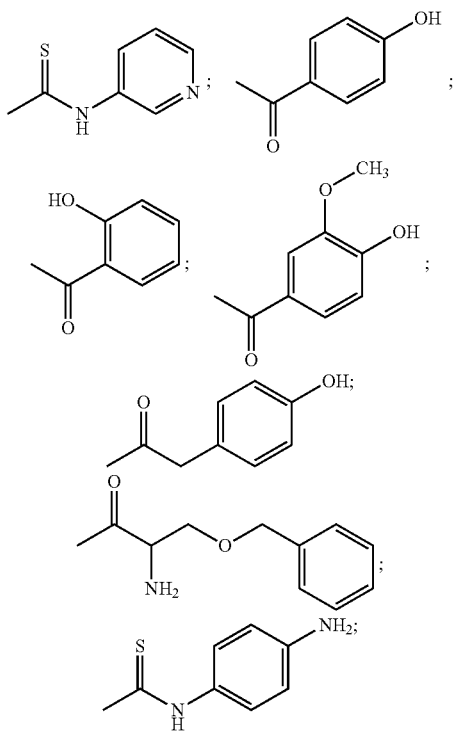

and optionally a combination thereof.

In a second aspect, the present invention concerns a composition comprising a cationic polymer of the invention and a molecule of interest non covalently associated with the polymer. The present invention also concerns a pharmaceutical composition comprising a cationic polymer of the invention, a therapeutically active molecule non covalently associated with the polymer and pharmaceutically acceptable excipients and/or carriers. The molecule may be selected from the group consisting of nucleic acid, protein, peptide, small chemical compound and drug. Preferably, the molecule is a nucleic acid. More preferably, the molecule is a nucleic acid selected from the group consisting of interfering RNA, antisense nucleic acid and ribozyme. The nucleic acid may be selected from the group consisting of small interfering RNA (siRNA), double-stranded RNA (dsRNA), double-stranded DNA (dsDNA), single-stranded RNA (ssRNA), single-stranded DNA (ssDNA), micro-RNA (miRNA), short hairpin RNA (shRNA), short hairpin DNA (shDNA) and DNA-RNA duplex. Preferably, the nucleic acid is a siRNA.

It is an object of the invention to provide new composition useful as oligonucleotide and nucleic acids transfection agents. The invention relates to the method of transfection of cells in vitro. The invention relates to a composition comprising polyamines modified by aromatic molecules such as above defined and either double stranded or single stranded nucleic acids in an aqueous solution.

In a further aspect, the present invention concerns a pharmaceutical composition as described above for the delivery of the therapeutically active molecule to a mammal, preferably a human being.

The compositions of the invention are useful for delivery of oligonucleotide to cells in vitro, ex-vivo and in vivo.

The present invention also concerns a method for delivering a molecule of interest to a cell, said method comprising contacting a composition of the invention with said cell. Preferably, the method is an in vitro or ex vivo method. Preferably, the cell is a mammalian cell, more preferably a human cell. The mammalian cell may be a tumoral cell, preferably a human tumoral cell.

The present invention further concerns the use of a composition of the invention for in vitro or ex vivo delivering the molecule of interest to a cell.

In another aspect, the present invention concerns the use of a cationic polymer of the invention, preferably a polyethylenimine, as vehicle or carrier for delivering a molecule of interest to a cell.

In another aspect, the present invention concerns the use of a cationic polymer of the invention, preferably a polyethylenimine, as transfection agent.

In a last aspect, the present invention concerns a method for preparing a pharmaceutical composition for delivering a therapeutically active molecule to a mammal, said method comprising mixing a cationic polymer of the invention with the therapeutically active molecule.

BRIEF DESCRIPTION OF THE DRAWINGS

FIG. 18: Electrostatic stability of the polyplexes at pH 7.8 (extracellular value) and pH 6.0 (endosomal value). siRNA polyplexes (100 nmol in EI of polymer, 0.7 µg siRNA) were incubated for 20 min with increasing amounts of heparin and release of siRNA was determined from agarose gel electrophoresis analyses.

FIG. 19: FIG. 19A. Hemolytic activity of the polymers. 100% hemolysis was obtained using triton X-100 (final concentration of 0.1% w/v) FIG. 19B. Effect of the polymer concentration on the cellular viability. Cell viability was monitored by measuring the cell metabolic activity (MTT assay).

FIG. 20.

FIG. 21.

DETAILED DESCRIPTION OF THE INVENTION

Figure 1:
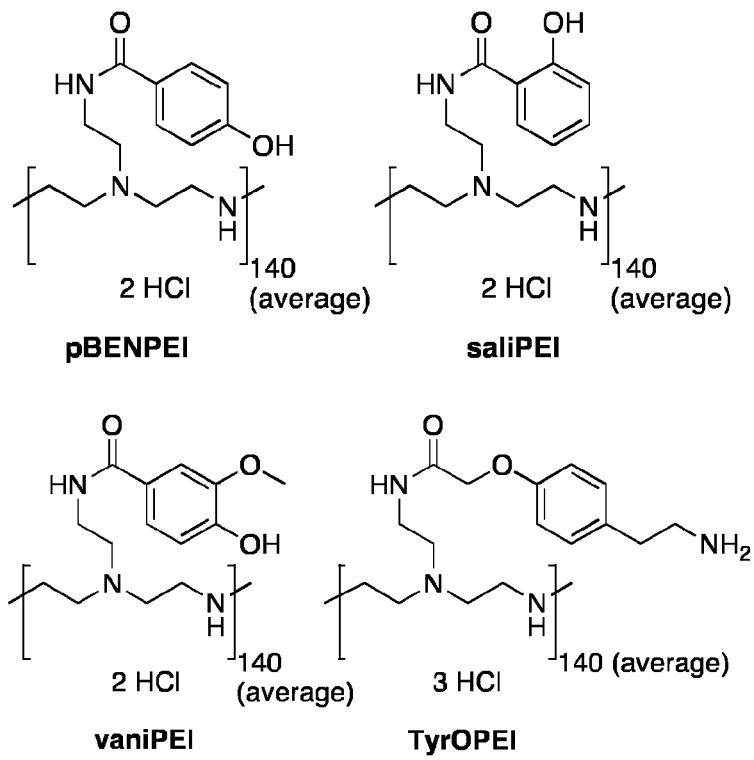
FIG. 1: Chemical structure of the polyethylenimines that were modified with aromatic groups via an amide linkage.

The present invention relates to the unexpected finding that replacement of one reacting aliphatic amine of the PEI with an other aliphatic one (provided by the aromatic alpha-aminoacids) is not necessary for obtention of an excellent siRNA delivery agent. This finding suggest that electrostatic forces are not as important as generally assumed for maintaining cohesion of siRNA polyplexes in biological media.

The present invention relates to a new class of cationic polymers that self-assemble with a pH-sensitive dissolution switch. More or less, the polymers aggregate at neutral pH and disaggregate at acidic pH. This new class of polymers correspond to cationic polymers having multiple amine functions modified or substituted by aromatic radical, but not an aromatic radical from an aromatic amino acid (i.e., not a tyrosyl radical). The polymer is a polyamine backbone.

The present invention relates to a cationic polymer, preferably a linear or branched polyethylenimine, having multiple amine functions modified or substituted by a radical X, wherein X is C(=Z)—R$_1$ wherein Z is S or O; and R1 is selected from the group consisting of

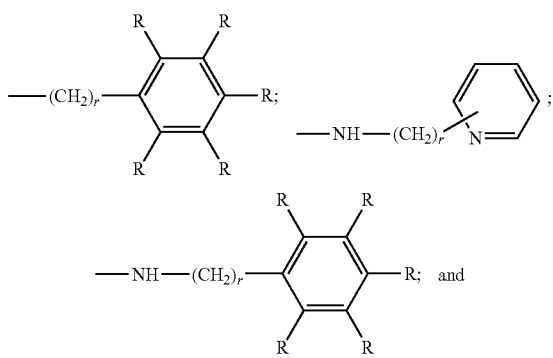

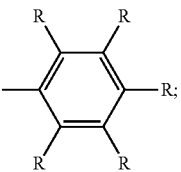

and optionally a combination thereof wherein r is an integer from 0 to 2, R are independently selected from the group consisting of H, OH, OCH$_3$, NH$_2$, O(CH$_2$CH$_2$O)$_m$H, and O(CH$_2$CH$_2$O)$_m$CH$_3$ with m being an integer between 1 and 500, preferably of H, OH, OCH$_3$, and NH$_2$.

Optionally, the pyridinyl cycle may be substituted by one or several substituents selected from the group consisting of OH, OCH$_3$, NH$_2$, O(CH$_2$CH$_2$O)$_m$H, and O(CH$_2$CH$_2$O)$_m$CH$_3$ with m being an integer between 1 and 500, preferably of 1. In a preferred embodiment, the pyridinyl cycle is not substituted.

Preferably, r is 0 or 1. More preferably, r is 0.

Preferably, at least 3 or 4 of the 5 R are H and the other R are selected from the group consisting of H, OH, NH$_2$, and OCH$_3$, more preferably of H, OH, and OCH$_3$. More particularly, 4 of the 5 R are H and the other R is OH in ortho, para or meta, preferably in ortho or para. Alternatively, 4 of the 5 R are H and the other R is NH$_2$ in ortho, para or meta, preferably in para. Otherwise, 3 of the 5 R are H and one R is OH and the other is OCH$_3$. Preferably, the OH is in ortho or para and the OCH$_3$ is in meta.

In a particular embodiment, the polymers or polyamines have been modified by an aromatic compound selected from the group comprising benzoic acid, pyridine isothiocyanate, benzyl, pyridine isocyanate, hydroxylbenzoic acid or the derivatives thereof.

In a first particular preferred embodiment, X is selected from the group consisting of

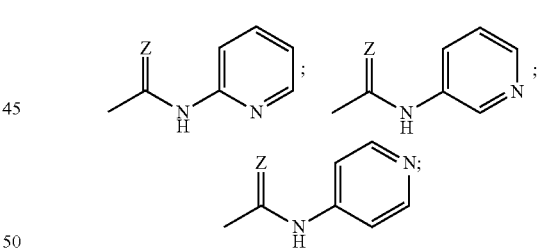

and optionally a combination thereof, wherein Z is O or S.

Optionally, the pyridinyl cycle may be substituted by one or several substituents selected from the group consisting of OH, OCH$_3$, NH$_2$, O(CH$_2$CH$_2$O)$_m$H, and O(CH$_2$CH$_2$O)$_m$CH$_3$ with m being an integer between 1 and 500, preferably of 1. In a preferred embodiment, the pyridinyl cycle is not substituted. In a most preferred embodiment, X is selected from the group consisting of

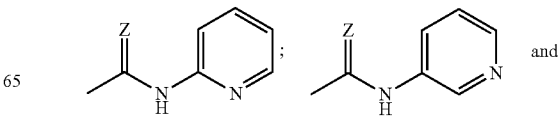

-continued

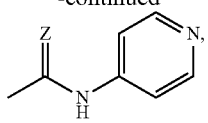

wherein Z is S or O. More preferably, Z is S.

In a most preferred embodiment, X is

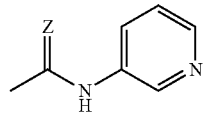

wherein Z is O or S. More preferably, Z is S.

In a second particular preferred embodiment, X is selected from the group consisting of

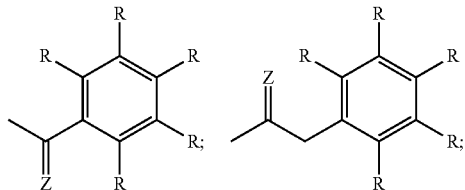

and optionally a combination thereof;

wherein Z is O or S and R is selected from the group consisting of H, OH, OCH$_3$, NH$_2$, O(CH$_2$CH$_2$O)$_m$H, and O(CH$_2$CH$_2$O)$_m$CH$_3$ with m being an integer between 1 and 500, preferably of H, OH, NH$_2$, and OCH$_3$, more preferably of H, OH, and OCH$_3$.

Preferably, X is selected from the group consisting of

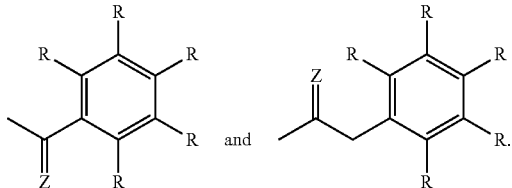

More preferably, Z is O and X is

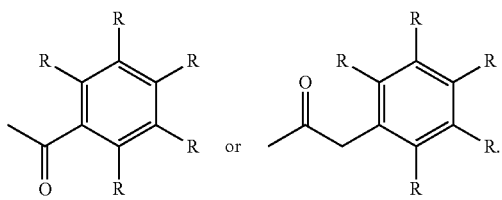

Preferably, at least 3 or 4 of the 5 R are H and the other R are selected from the group consisting of H, OH, NH$_2$, and OCH$_3$, more preferably of H, OH, and OCH$_3$. More particularly, 4 of the 5 R are H and the other R is OH in ortho, para or meta, preferably in ortho or para. Alternatively, 4 of the 5 R are H and the other R is NH$_2$ in ortho, para or meta, preferably in para. Otherwise, 3 of the 5 R are H and one R is OH and the other is OCH$_3$. Preferably, the OH is in ortho or para and the OCH$_3$ is in meta.

More preferably, X is selected from the group consisting of

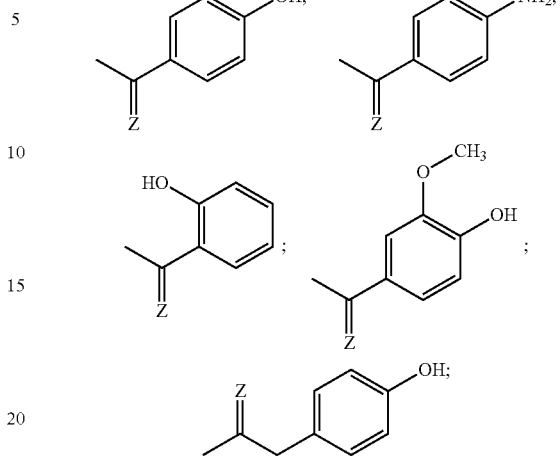

and optionally a combination thereof.

Still more preferably, X is selected from the group consisting of

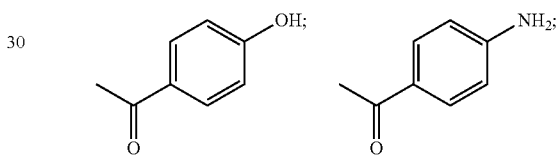

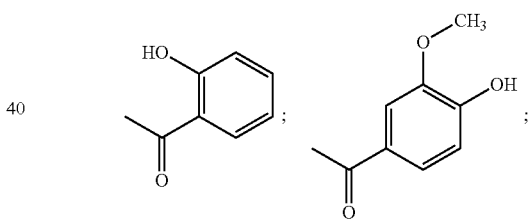

and optionally a combination thereof.

In a third particular preferred embodiment, R1 is

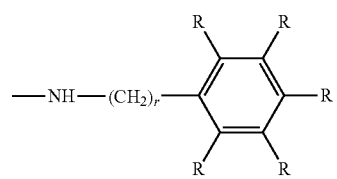

with 4 of the R being H and the other R being NH2, preferably in para. More preferably, r is 0. Still more preferably, Z is S.

Accordingly, in a preferred embodiment, X is

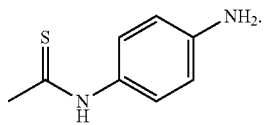

In a fourth particular preferred embodiment, X is C(=Z)—R1 and $R_1$ is

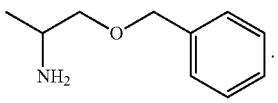

Preferably, Z is O. Accordingly, in a preferred embodiment, X is

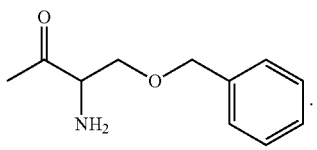

In a very particular and preferred embodiment, X is selected from the group consisting of

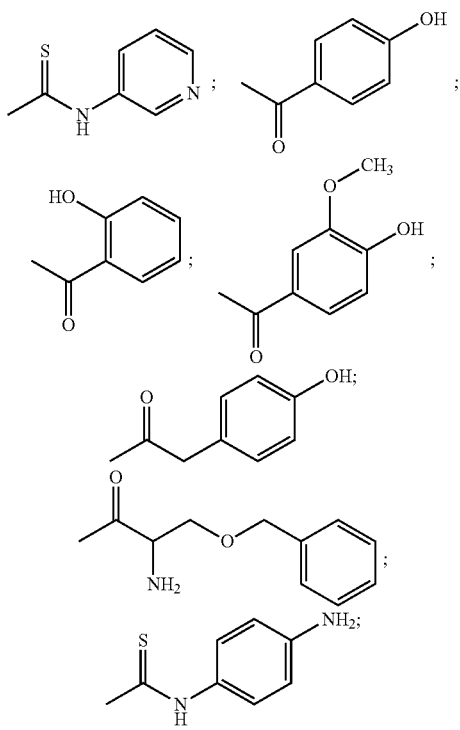

and optionally a combination thereof.

In regard to the cationic polymers, suitable polyamines comprise branched and linear polyethylenimine, dendrimers, cationic proteins, histones, protamines or one of these polymers modified with alpha-amino-acids. In a preferred embodiment, the cationic polymer is selected from the group consisting of a linear polyethylenimine, a branched polyethylenimine, a polydendrimer or dendrimer, a chitosan, a polyallylamine, a polyaminoester, a polylysine, a polyornithine, a polyhistidine, a polyarginine, a polylysine-rich protein (such as protamine or one of the histones), a peptide and a polyamine. More preferably, the cationic polymer is selected from the group consisting of a linear polyethylenimine, a branched polyethylenimine, a polydendrimer or dendrimer, and a chitosan.

The molecular weight of the polyamines or cationic polymers used according to the invention is more generally above 400 Da. Preferably, the polyamines or cationic polymers are selected in the group from 1,500 Da to 200,000 Da.

In a more preferred embodiment, the cationic polymer is a linear polyethylenimine or a branched polyethylenimine. In a most preferred embodiment, the cationic polymer is a branched polyethylenimine. In particular, any particular embodiment of the radical X is contemplated by the present invention in combination with such a polyethylenimine.

For instance, when the polymer is a polyethylenimine, the number of ethylenimine units, generally called "n" in the present disclosure, is from 2 to 5000, preferably from 10-2000, more preferably from 10-500, and still more preferably from 10-200.

The term "p" as used herein defines the frequency or degree of modification or substitution of the polymer. For instance, when p is 0.1, it means that 10% of the basic unit are modified. In the case of polyethylenimine, it means that 10% of the ethylenimine unit are linked to a radical X.

Accordingly, the degree of modification of the polymer in the composition of the invention varies from 1 to 100%. More preferably, the degree of modification is in the 15 to 60% range, preferably in the 20 to 50% range. Therefore, in the contemplated polymers, the amine functions are modified or substituted by a radical X at a ratio of p from 0.01 to 1 or from 0.1 to 0.9, preferably from 0.15 to 0.5, more preferably from 0.2 to 0.4, still more preferably about 0.30

More preferably, when the cationic polymer is a linear or branched polyethylenimine, then p is between 0.15 to 0.50, preferably between 0.2-0.4, and still more preferably about 0.3.

As used in this specification, the term "about" refers to a range of values±10% of the specified value. For instance, "about 1" means from 0.9 to 1.1 when 10% is considered and from 0.95 to 1.05 when 5% is considered.

In a preferred embodiment, the polymer is a polyethylenimine, linear or branched. Such polymers are well-known in the art and are commercially available, for instance from Sigma-Aldrich (France), from Polysciences Inc etc. In a preferred embodiment, the polymer is a branched polyethylenimine. A standard branched polyethylenimine may comprise 20-30% of primary amines, 40-60% of secondary amines and 20-30% of tertiary amines.

In a particular, the modified amines are only or mainly with the primary amines. Alternatively, the modified amines are both primary and secondary amines.

Accordingly, when the polymer is a polyethylenimine, the polymer can be represented by the following formula

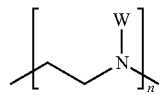

wherein

W is selected from the group consisting of H, X, —(CH$_2$)$_2$—NHX, and —(CH$_2$)$_2$—NH$_2$; and n is an integer from 10 to 2000, preferably 10 to 500, and more preferably 10 to 200;

with a ratio of X and —(CH$_2$)$_2$—NHX being p.

In a preferred embodiment, W is selected from the group consisting of H, —(CH$_2$)$_2$—NHX, and —(CH$_2$)$_2$—NH$_2$, with a ratio of —(CH$_2$)$_2$—NHX being p.

In a preferred embodiment, when the polymer is a polyethylenimine, the polymer can be represented by the following formula

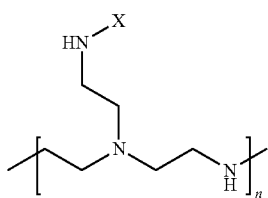

wherein n is an integer from 10 to 500, preferably from 10 to 200, more preferably from 14 to 150; and X is as defined above within any and each of the particular embodiments.

In a very particular and preferred embodiment, when the polymer is a polyethylenimine, the polymer can be represented by one formula selected from the group consisting of

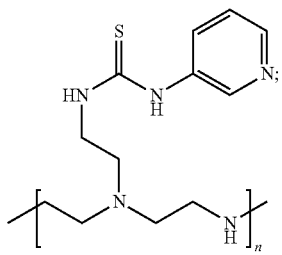

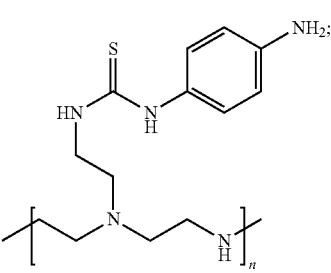

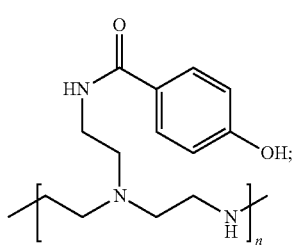

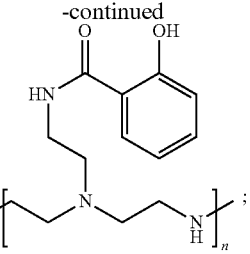

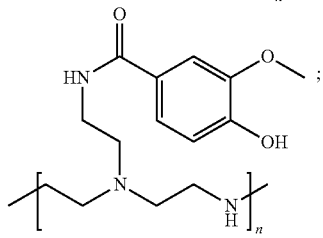

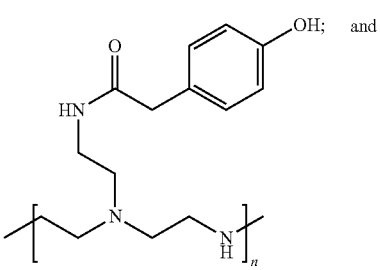

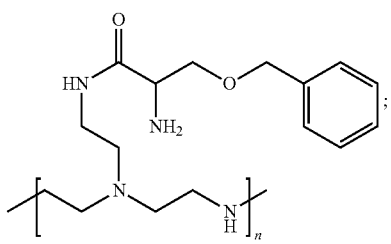

wherein n is an integer from 10 to 500, preferably from 10 to 200, more preferably from 14 to 150.

The methods for preparing the polymers of the present invention are well-known by the one skilled in the art. In particular, the reaction conditions may be adjusted in order to modify only or mainly with the primary amines, both with the primary and secondary amines. In a preferred embodiment using branched polyethylenimine, the reaction conditions may be adjusted in order to modify only or mainly with the primary amines. Preparation of these polymers may be performed using almost any coupling reagents (Valeur and Bradley, 2009). The preparation of polymers of the present invention is illustrated in the examples 1 and 2 of the present application.

Alternatively, the invention relates to cationic polymers of formula

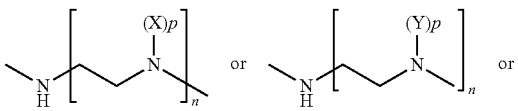

-continued

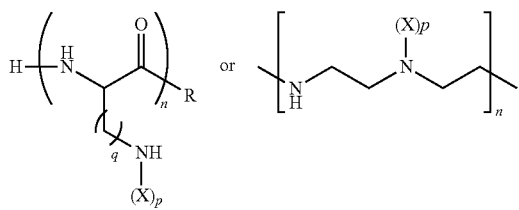

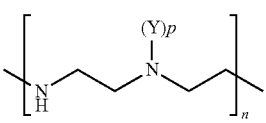

wherein

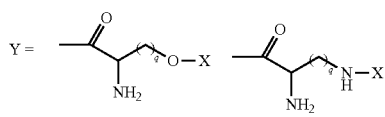

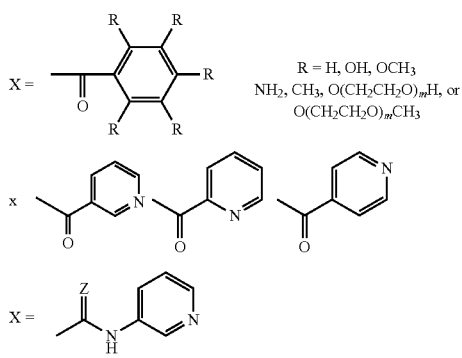

p: 0.1 to 0.9  m: 1 to 500
n: 2 to 5000  q: 1 to 5
Z = O or S

More preferably, the invention relates to cationic polymers of formula

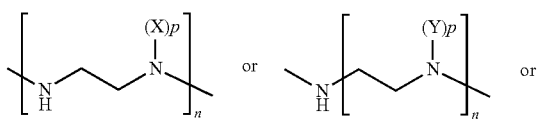

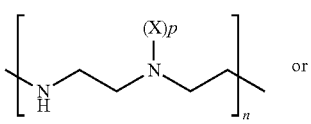

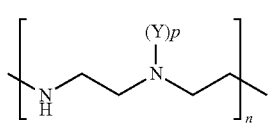

-continued wherein

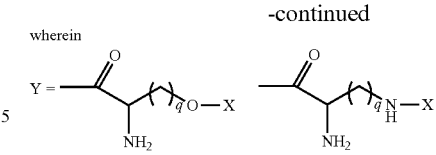

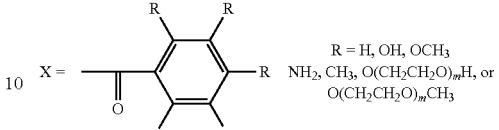

p: 0.1 to 0.9  m: 1 to 500
n: 2 to 5000  q: 1 to 5

Z = O or S

The polymer of the invention may be in the form of salt, in particular pharmaceutically acceptable salt. The term "pharmaceutically acceptable salt" refers to salts which are non-toxic for a patient and suitable for maintaining the stability of the polymer and allowing the delivery of said polymer to target cells or tissue. Pharmaceutically acceptable salts are well known in the art (Berge et al., 1977). Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, 3-phenylpropionate, phosphate, picrate, pivalate, propionate, stearate, succinate, sulfate, tartrate, thiocyanate, p-toluenesulfonate, undecanoate, valerate salts, and the like.

The present invention also concerns a composition comprising a cationic polymer according to the invention and a molecule of interest non covalently associated with said polymer. Preferably, the cationic polymer is a polyethylenimine.

The present invention further concerns a pharmaceutical composition comprising a cationic polymer according to the invention, a therapeutically active molecule non covalently associated with said polymer, and pharmaceutically acceptable excipients and/or carriers.

The pharmaceutical composition of the invention is formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

Possible pharmaceutical compositions include those suitable for oral, rectal, topical (including transdermal, buccal and sublingual), parenteral (including subcutaneous, intramuscular, intratumoral, intravenous and intradermal) administration. For these formulations, conventional excipient can be used according to techniques well known by those skilled in the art.

The compositions for parenteral administration are generally physiologically compatible sterile solutions or suspensions which can optionally be prepared immediately before use from solid or lyophilized form. Adjuvants such as a local anesthetic, preservative and buffering agents can be dissolved in the vehicle and a surfactant or wetting agent can be included in the composition to facilitate uniform distribution of the active ingredient.

For oral administration, the composition can be formulated into conventional oral dosage forms such as tablets, capsules, powders, granules and liquid preparations such as syrups, elixirs, and concentrated drops.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used.

Preferably, the pharmaceutical composition of the invention is suitable for parenteral administration.

Pharmaceutical composition according to the invention may be formulated to release the complex containing the cationic polymer of the invention and the therapeutically active molecule, substantially immediately upon administration or at any predetermined time or time period after administration.

The molecule non covalently associated with the polymer of the invention may be selected from the group consisting of nucleic acid, protein, peptide, lipid, carbohydrate, small chemical compound and drug, preferably from the group consisting of nucleic acid, protein, peptide, small chemical compound and drug, more preferably from the group consisting of nucleic acid, protein and peptide. Preferably, the molecule bears one or several anionic groups and can interact with the cationic polymer of the invention through electrostatic interactions. The term "small chemical compound" as used herein refers to a molecule with a molecular weight of less than 5 kDa.

In an embodiment, the molecule is a drug. Examples of such drug include, but are not limited to, bisphosphonate compounds such as Etidronate, Clodronate, Tiludronate, Pamidronate, Neridronate, Olpadronate, Alendronate, Ibandronate, Risedronate or Zoledronate; antitumoral drugs such as taxol, docetaxel, doxorubicin and the like In another embodiment, the molecule is a protein. Examples of such protein include, but are not limited to antibodies, antibody fragments, nuclear protein or p53 enzyme.

In a preferred embodiment, the molecule is a nucleic acid. For instance, the nucleic acid may be a vector such as a plasmid.

The nucleic acid may be a single or double stranded molecule of at least 5 nucleotides in length, preferably from 5 to 10,000 nucleotides in length, more preferably from 5 to 200 nucleotides in length, even more preferably from 5 to 50 nucleotides in length.

The nucleic acid may be selected from the group consisting of small interfering RNA (siRNA), double-stranded RNA (dsRNA), double-stranded DNA (dsDNA), single-stranded RNA (ssRNA), single-stranded DNA (ssDNA), micro-RNA (miRNA), short hairpin RNA (shRNA), short hairpin DNA (shDNA) and DNA-RNA duplex. The nucleic acid may be linear or circular.

Preferably, the nucleic acid selected from the group consisting of interfering RNA, antisense nucleic acid or ribozyme.

The term "RNAi" or "interfering RNA" means any RNA which is capable of down-regulating the expression of a targeted protein. It encompasses small interfering RNA (siRNA), double-stranded RNA (dsRNA), single-stranded RNA (ssRNA), micro-RNA (miRNA), and short hairpin RNA (shRNA) molecules. A number of patents and patent applications have described, in general terms, the use of RNAi molecules to inhibit gene expression, for example, WO 99/32619, US 20040053876, US 20040102408 and WO 2004/007718. In a preferred embodiment, the RNAi molecule is a siRNA of at least about 15-50 nucleotides in length, preferably about 20-30 base nucleotides, more preferably about 20-25 nucleotides in length.

Antisense nucleic acid can also be associated to the cationic polymer of the invention. The antisense nucleic acid is complementary to all or part of a sense nucleic acid encoding a targeted polypeptide e.g., complementary to the coding strand of a double-stranded cDNA molecule or complementary to an mRNA sequence, and it thought to interfere with the translation of the target mRNA. An antisense nucleic acid can be, for example, about 5, 10, 15, 20, 25, 30, 35, 40, 45 or 50 nucleotides in length. Particularly, antisense RNA molecules are usually 18-50 nucleotides in length. Antisense nucleic acid may be modified to have enhanced stability, nuclease resistance, target specificity and improved pharmacological properties. For example, antisense nucleic acid may include modified nucleotides designed to increase the physical stability of the duplex formed between the antisense and sense nucleic acids, e.g., phosphorothioate derivatives and acridine substituted nucleotides.

The nucleic acid associated to the cationic polymer of the invention may also be a ribozyme molecule. Ribozymes are catalytic RNA molecules with ribonuclease activity which are capable of cleaving a single-stranded nucleic acid, such as an mRNA, to which they have a complementary region. Thus, ribozymes can be used to catalytically cleave mRNA transcripts to thereby inhibit translation of the protein encoded by the mRNA.

In a particularly preferred embodiment, the molecule is a siRNA.

siRNA and oligonucleotide, respectively, can contain suitable modifications to stabilize it against degradation or to increase its affinity for its biological target. The oligonucleotides sequences can contains deoxyribonucleotides, ribonucleotides or nucleotids analogs (Verma and Eckstein, 1998) and inter-nucleotide linkages such as methylphosphonate, morpholino phosphorodiamidate, phosphorothioate and amide.

Nucleic acid associated with the polymer of the invention may be synthesized and/or modified by methods well established in the art. Chemical modifications may include, but are not limited to 2' modifications (e.g. 2'-fluo, 2'-methoxy), introduction of non-natural bases, covalent attachment to a ligand, and replacement of phosphate linkages with thiophosphate linkages.

The concentration of oligonucleotide in said compositions of the invention vary from picomolar to millimolar.

Preferably, the cationic polymer to molecule ratio is from 2 to 5000. In a particular embodiment, the molecule is a nucleic acid and the cationic polymer to nucleic acid ratio is from 2 to 5000, preferably from 2 to 1000. In a more particular embodiment, the molecule is a siRNA and the cationic polymer to siRNA ratio is from 2 to 500, preferably from 10 to 200.

The composition of the invention may comprise one or several different cationic polymers according to the invention. The composition may also comprise one or several different molecules. In an embodiment, the composition comprises one type of complex containing a polymer of the invention and a molecule. In another embodiment, the composition comprises several types of complexes. In this embodiment, complexes may comprise (1) the same polymer of the invention associated with different molecules, (2) different polymers of the invention associated with the same molecule, or (3) different polymers of the invention associated with different molecules.

The composition of the invention may further comprise one or several additional substances such as polyethyleneglycol (PEG), Pluronic® (BASF), hyaluronic acid, saccharides, polysaccharides, polyvinyl alcohol (PVA), peptides, proteins, vitamins or drugs.

The present invention also concerns a pharmaceutical composition as described above for the delivery of the therapeutically active molecule to a subject.

As used in this specification, the term "subject" or "patient" refers to an animal, preferably to a mammal such as human, dogs, cats, horses, cows, pigs, sheep and non-human primates. Preferably, this term refers to a human, including adult, child and human at the prenatal stage.

Preferably, the therapeutically active molecule is a nucleic acid, more particularly a siRNA or oligonucleotide.

In a further aspect, the present invention further concerns a method for preparing a pharmaceutical composition for delivering a therapeutically active molecule to a subject, said method comprising mixing a cationic polymer of the invention with the therapeutically active molecule.

All embodiments disclosed above for the cationic polymer and for the compositions of the invention are also encompassed in this aspect.

The cationic polymer may be mixed with the therapeutically active molecule in an aqueous solution having a pH value of at least 4.5, preferably about 7.5. In an embodiment, the cationic polymer is mixed with the therapeutically active molecule in an aqueous solution suitable for physiological applications such as physiological serum, a 2 to 10% w/v glucose solution, a 4 to 10% sucrose solution and any solution isotonic to body fluids.

Before incubation, it could be necessary to adjust the pH value to allow the formation of the complexes cationic polymer/therapeutically active molecule. Preferably, the pH value of the aqueous solution comprising the polymer and the molecule is adjusted to a value greater than 6.5, preferably, greater than 7, more preferably about 7.5.

The mix is incubated to allow the formation of the complexes. Preferably, incubation conditions are adjusted to obtain complexes having diameters of a least 10 nm but below 20,000 nm. Conditions may be easily adjusted by the skilled person. Size of complexes may be adjusted by varying the incubation medium composition, the stoichiometry between the cationic polymer and the oligonucleotide, the incubation time and the temperature. In a particular embodiment, the mixture is incubated for about 0.1 h at room temperature in 4.5% glucose solution, at room temperature (generally above 4° C., below 40° C. preferably at 20° C.) to provide complexes of 80 nm in diameter.

The cationic polymer and the therapeutically active molecule can be mixed before the packaging of the pharmaceutical composition or just before administration to the subject.

In another aspect, the present invention also concerns a kit for preparing a composition for delivering a molecule of interest to a cell, said kit comprising at least one cationic polymer of the invention and a leaflet providing guidelines to use such a kit. Optionally, the kit may further comprise a buffer and/or a 2 to 10% glucose solution and/or a cell culture medium and/or solution isotonic to biological fluids. All embodiments disclosed above for the cationic polymer and for the compositions of the invention are also encompassed in this aspect.

In a further aspect, the present invention also concerns a method for delivering a molecule of interest to a cell, said method comprising contacting a composition according to the invention with said cell.

Preferably, the cell is a mammalian cell, more preferably a human cell. In a particular embodiment, the cell is a tumoral cell, preferably a human tumoral cell.

The method may be an in vivo, in vitro or ex vivo method, preferably an in vitro or ex vivo method. In vitro or ex vivo delivery of molecules, in particular oligonucleotides, may be carried out in medium containing adherent cells or cells in suspension.

All embodiments disclosed above for the compositions of the invention are also encompassed in this aspect.

In another aspect, the present invention concerns a method for delivering a molecule of interest, preferably a therapeutically active molecule, to a subject, said method comprising administering to said subject a composition, preferably a pharmaceutical composition, comprising a cationic polymer of the invention, preferably a polyethylenimine, the molecule of interest non covalently associated with the cationic polymer, and optionally pharmaceutically acceptable excipients and/or carriers. All embodiments disclosed above for the cationic polymer and for the composition of the invention are also encompassed in this aspect.

The present invention further concerns the use of a composition according to the invention for in vitro or ex vivo delivering a molecule of interest to a cell.

Preferably, the cell is a mammalian cell, more preferably a human cell. In a particular embodiment, the cell is a tumoral cell, preferably a human tumoral cell.

All embodiments disclosed above for the compositions of the invention are also encompassed in this aspect.

The present invention further concerns the use of a cationic polymer according to the invention as vehicle or carrier for delivering a molecule of interest to a cell. All embodiments disclosed above for the cationic polymer and for the compositions of the invention are also encompassed in this aspect.

The present invention further concerns the use of a cationic polymer according to the invention as transfection agent. All embodiments disclosed above for the cationic polymer of the invention are also encompassed in this aspect. Preferably, the cationic polymer of the invention is used to transfect a siRNA.

The following examples are given for purposes of illustration and not by way of limitation.

EXAMPLES

Example 1

Materials and Methods

Materials

Chemicals were purchased from Sigma-Aldrich (St Quentin, France). Branched PEI 25 kDa (40,872-7, batch 09529KD-466) and branched PEI 1800 Da (408700, batch 0726LH) were from Aldrich (St Quentin, France). PEI 1800 Da was supplied as a 50% aqueous solution and was dried by several coevaporation under reduced pressure with methanol. Before use, dialysis membranes were soaked in MilliQ water (200 mL, 3 times, 8 h each) to remove preservatives. Chemical synthesis and work-ups were performed under a chemical fume hood. Experiments involving cell lines were performed according to the biosafety level 2 guidance. Water was deionized on a Millipore Milli-Q apparatus. Buffer and water were sterilized by filtration through 0.22 μm pore membrane and were kept sterile by working under a class II microbiological safety cabinet. All other chemicals were at least of analytical grade and were used as supplied. UV/Vis analysis was performed on a Varian Cary 100Bio Spectrometer. NMR spectra were performed on a Bruker DPX 400 MHz spectrometer. The level of PEI modification was evaluated from NMR data.

Synthesis

Note: The modification degree of the polymer was determined relative to ethylenimine residues by integration of $^1$H NMR signals and was of 30+/−5% for all polymer otherwise indicated. Quantities of polymers were given in ethylenimine residue. Calculation of the molecular mass of the novel polymers was done using the following formula: $MM_{novelPEI} = MM_{PEI} + C/100(MM_{grafted\ molecule} - MM_{water\ if\ applied})$ C: percentage of grafted molecule per ethylenimine. MM: molecular mass.

O-acetic Acid, N-Boc-tyramine

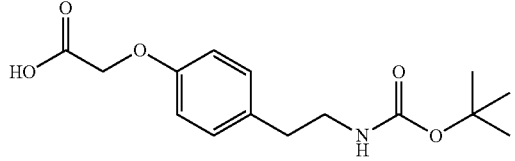 [SMILES: CC(C)(C)OC(=O)NCCc1ccc(OCC(=O)O)cc1]

Cesium carbonate (6 g, 18.4 mmol) and then ethyl bromoacetate (3 mL) were slowly added to a solution of N-Boc tyramine (4.5 g, 18.9 mmol) in anhydrous DMF (20 mL). The reaction was stirred at room temperature for 4 h and was then diluted with ethylacetate (150 mL). The organic phase was washed with citric acid 0.5M (200 mL), dried over MgSO$_4$ and evaporated under reduced pressure. The oil was then dissolved in methanol (30 mL) and treated with aqueous NaOH 2M (10 mL) for 30 min at 60° C. Evaporation of the methanol under reduced pressure. The residue was dissolved in water (200 mL). The aqueous phase was then washed twice with ethylacetate (200 mL), acidified with citric acid 10% (200 mL) and the compound was extracted with ethyl acetate. The organic phase was then washed once with water, dried over MgSO$_4$ and the solvent was evaporated under reduced pressure to give the compound as white crystals (4.5 g, 15.24 mmol, 80% yield). $^1$H NMR (CDCl$_3$) δppm: 1.44 (s, t, 9H), 2.1 (s br, 2H), 3.2-3.3 (m, 2H), 4.6 (s, 2H), 6.8 (d, J=8.0 Hz, 2H), 7.1 (s, 2H), 9.6 (s br, 1H). $^{13}$C NMR (CDCl$_3$) δppm: 28.3, 35.4, 41.8, 65.0, 79.6, 114.7, 129.9, 132.2, 156.2, 172.8. ES-MS: (M calculated for C$_{15}$H$_{21}$NO$_5$) 294.1 ([M-H$^+$]).

O—(N-succinimidyl Acetate), N-Boc-tyramine

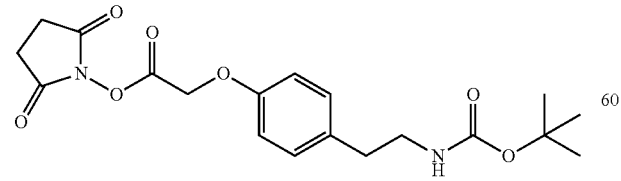

N-methyl-morpholine (1.84 mL, 16.76 mmol) was added at room temperature to a solution of O-acetic acid N-Boc tyramine (4.5 g, 15.24 mmol) and N,N'-disuccinimidyl carbonate (4.3 g, 16.76 mmol) in anhydrous acetonitrile (150 mL). After 12 h of stirring, the mixture was diluted with ethylacetate (200 mL). The organic phase was washed with citric acid 5% (100 mL), dried over MgSO$_4$ and the solvent was evaporated under reduced pressure. The residue was then subjected to a silica gel chromatography (elution CH$_2$Cl$_2$, gradient of 1 to 5% ethanol) to give the product (3.8 g, 60% yield). $^1$H NMR (CDCl$_3$) δppm: 1.44 (s, t, 9H), 2.1 (t, 2H), 2.85 (, 4H), 3.2-3.3 (m, 2H), 4.6 (s, 2H), 6.8 (d, J=8.4 Hz, 2H), 7.15 (d, J=8.4 Hz, 2H). $^{13}$C NMR (CDCl$_3$) δppm: 25.6, 28.3, 35.4, 41.8, 60.4, 79.3, 114.8, 129.9, 133.0, 155.9, 164.7, 168.6. ES-MS: (M calculated for C$_{19}$H$_{24}$N$_2$O$_7$) found: 293.0 ([MH$_2$-Boc]$^+$).

Succinimidyl Ester of Vanillic Acid

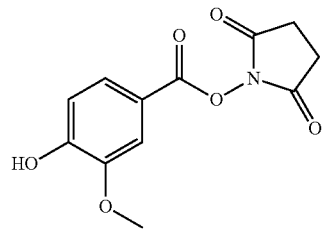

Chemical formula: C$_{12}$H$_{11}$NO$_6$
Exact mass: 265,0586
Molecular weight: 265,2188

A solution of N,N'-Dicyclohexylcarbodiimide (20 g, 97 mmol) in CH$_2$Cl$_2$ (2.5 mL) was added dropwise and at 0-4° C. to a solution of N-hydroxysuccinimide (8.9 g, 77 mmol) and vanillic acid (11.8 g, 70 mmol) in ethylacetate (80 mL) DMF (20 mL). The reaction mixture was then stirred overnight at room temperature and the dicyclohexylurea was removed by filtration and washed with ethyl acetate (100 mL). The organic phase was washed with saturated NaCl (100 mL), saturated NaHCO$_3$ (twice 100 mL) and saturated NaCl (100 mL). The organic phase was then dried over MgSO$_4$ and the solvent was removed under reduced pressure to give the product as a yellow solid (16.5 g; 70% yield). $^1$H NMR (CDCl$_3$) δppm: 2.9 (s, 4H), 3.9 (s, 3H), 6.9 (d, J=8.4 Hz, 1H), 7.55 (d, J=2.0 Hz, 1H, 7.75 (dd, J=2.0 Hz, J=8.4 Hz, 1H), 8.0 (s, 1H). $^{13}$C NMR (CDCl$_3$) δppm: 25.7, 56.2, 112.4, 114.8, 116.5, 125.9, 146.7, 152.2, 161.5, 169.5. ES-MS: (M calculated for C$_{12}$H$_{11}$NO$_6$: 265.0586) found: 288.04875 ([MNa]$^+$).

Succinimidyl Ester of Salicylic Acid

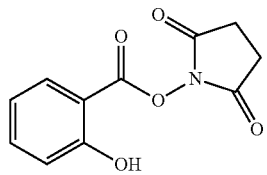

Chemical formula: C$_{11}$H$_9$NO$_5$
Exact mass: 235,0481
Molecular weight: 235,1929

A solution of N,N'-Dicyclohexylcarbodiimide (10.9 g, 53 mmol) in CH$_2$Cl$_2$ (5 mL) was added dropwise and at 0-4° C.

to a solution of N-hydroxysuccinimide (6.19 g, 53.8 mmol) and salicylic acid (44.7 mmol) in DMF (30 mL). The reaction mixture was then stirred overnight at room temperature and the dicyclohexylurea was removed by filtration and washed with ethyl acetate (200 mL). The organic phase was washed with saturated NaHCO$_3$ (twice 200 mL), citric acid 5% (200 mL) and saturated NaCl (200 mL). The organic phase was then dried over MgSO$_4$ and the solvent was removed under reduced pressure to give the product as a yellow solid (10.1 g, 95% yield). $^1$H NMR (CDCl$_3$) δppm: 2.9 (s, 4H), 6.95 (t, J=7.2 Hz, 1H), 7.05 (d, J=8.0 Hz, 1H), 7.58 (td, J=7.2 Hz, J=1.6 Hz, 1H), 8.0 (dd, J=8.0 Hz, J=1.6 Hz, 1H). $^{13}$C NMR (CDCl$_3$) δppm: 25.6, 108.1, 118.0, 120.0, 130.1, 137.9, 161.9, 165.0, 169.1. ES-MS: (M calculated for C$_{11}$H$_9$NO$_5$: 235.0481) found: 258.03771 ([MNa]$^+$).

Succinimidyl Ester of 4-hydroxybenzoic Acid

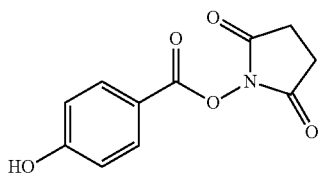

Chemical formula: C$_{11}$H$_9$NO$_5$
Exact mass: 235,0481
Molecular weight: 235,1929

A solution of N,N'-Dicyclohexylcarbodiimide (33 g, 160 mmol) in CH$_2$Cl$_2$ (20 mL) was added dropwise and at 0-4° C. to a solution of N-hydroxysuccinimide (18.5 g, 160 mmol) and 4-hydroxybenzoic acid (20.2 g, 146 mmol) in DMF (60 mL) and ethyl acetate (60 mL). The reaction mixture was then stirred overnight at room temperature and the dicyclohexylurea was removed by filtration and washed with ethyl acetate (150 mL). The organic phase was washed with saturated NaHCO$_3$ (twice 200 mL), citric acid 5% (200 mL) and saturated NaCl (200 mL). The organic phase was then dried over MgSO$_4$ and the solvent was removed under reduced pressure to give the product as a yellow solid (27 g, 78% yield). $^1$H NMR (CDCl$_3$) δppm: 2.9 (s, 4H), 6.88 (d, J=8.8 Hz, 2H), 7.97 (d, J=8.8 Hz, 2H). $^{13}$C NMR (CDCl$_3$) δppm: 25.6, 115.7, 133.1, 161.7, 163.3, 169.9. ES-MS: (M calculated for C$_{11}$H$_9$NO$_5$: 235.0481) found: 258.03785 ([MNa]$^+$).

Succinimidyl Ester of 4-hydroxyphenylacetic Acid

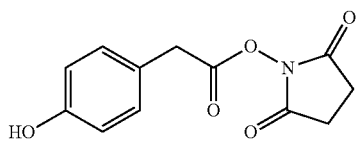

Chemical formula: C$_{12}$H$_{11}$NO$_5$
Exact mass: 249,0637
Molecular weight: 249,2194

A solution of N,N'-Dicyclohexylcarbodiimide (4.14 g, 20 mmol) in CH$_2$Cl$_2$ (5 mL) was added dropwise and at 0-4° C. to a solution of N-hydroxysuccinimide (2.31 g, 20 mmol) and 4-hydroxyphenylacetic acid (2.55 g, 16.77 mmol) in DMF (20 mL) and ethyl acetate (20 mL). The reaction mixture was then stirred overnight at room temperature and the dicyclohexylurea was removed by filtration and washed with ethyl acetate (150 mL). The organic phase was washed with saturated NaHCO$_3$ (twice 100 mL), citric acid 5% (100 mL) and saturated NaCl (200 mL). The organic phase was then dried over MgSO$_4$ and the solvent was removed under reduced pressure to give the product as a yellow solid (4.0 g, 95% yield). $^1$H NMR (CDCl$_3$) δppm: 2.8 (s, 4H), 3.8 (s, 2H), 6.88 (d, J=6.4 Hz, 2H), 7.15 (d, J=6.4 Hz, 2H). $^{13}$C NMR (CDCl$_3$) δppm: 25.6, 36.8, 115.7, 122.5, 130.4, 156.2, 167.3, 169.3. ES-MS: (M calculated for C$_{12}$H$_{11}$NO$_5$: 249.0637) found: 272.05392 ([MNa]$^+$).

N-3-pyridyl-, N'-PEI-thiourea 15% (PyPEI 15%)

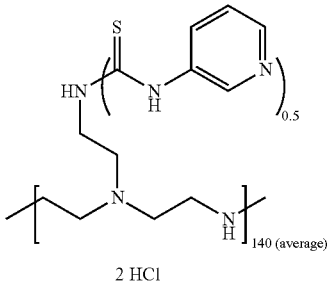

2 HCl

A solution of 3-pyridyl isothiocyanate (230 mg; 1.73 mmol) in CH$_2$Cl$_2$ (50 mL) was added dropwise and at room temperature to a solution of polyethylenimine (500 mg; 11.62 mmol) in CH$_2$Cl$_2$ (40 mL). After 30 minutes reaction, TLC indicated full consumption of the isothiocyanate. The solvent was then evaporated under reduced pressure. The residue was dissolved in water (40 mL) and the solution was adjusted to pH 4.0 by addition of hydrochloric acid 3M. Dialysis using a SpectraPor 12-14 kDa membrane against water (1 L volume; 2 changes over 48 h) and freeze drying gave 515 mg of PEI-Isothiourea-Pyridine 15%. The level of PEI modification was evaluated from NMR data. $^1$HNMR (D$_2$O) δppm: 4.02-2.65 (m, 4H, NHCH$_2$CH$_2$NH) 4.24 (t, 0.3H, CH$_2$NCS), 7.82 (m, 0.15 H, CHaro), 9.1-8.1 (m, 0.3H,CHaro).

N-3-pyridyl-, N'-PEI-thiourea (PyPEI)

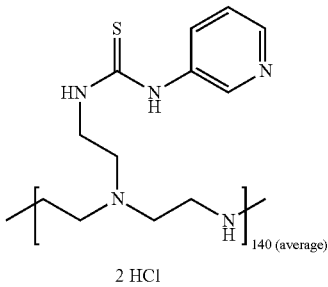

2 HCl

A solution of 3-pyridyl isothiocyanate (460.4 mg; 3.46 mmol) in CH$_2$Cl$_2$ (40 mL) was added dropwise and at room temperature to a solution of polyethylenimine (500 mg; 11.62 mmol) in CH$_2$Cl$_2$ (40 mL). After 30 minutes reaction, TLC indicated full consumption of the isothiocyanate. The solvent was then evaporated under reduced pressure. The residue was dissolved in water (40 mL) and the solution was adjusted to pH 4.0 by addition of hydrochloric acid 3M. Dialysis using a SpectraPor 12-14 kDa membrane against water (1 L volume; 2 changes over 48 h) and freeze-drying gave 650 mg of PEI-Isothiourea-Pyridine 25%. $^1$HNMR (D$_2$O) δppm: 3.95-2.5 (m, 4H, NHCH$_2$CH$_2$NH), 4.2 (t, 0.5H, CH$_2$NCS), 7.5 (m, 0.25H, CHaro), 7.86 (m, 0.25H, CHaro), 8.45 (m, 0.5H, CHaro). λ$_{max}$(ε calculated for ethylenime unit): 245 nm (2660 M$^{-1}$.cm$^{-1}$).

4-hydroxybenzamide-PEI (13%) (pBENPEI 15%)

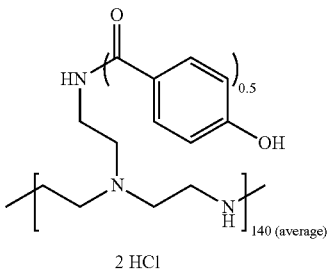

2 HCl

A solution of freshly prepared 4-hydroxybenzoic acid (476 mg; 3.45 mmol) and BOP (1.7 g; 3.8 mmol) in DMF (20 mL) was added dropwise and at room temperature to a solution of PEI (1 g, 23.2 mmol) in DMF (30 mL). After 2 hours under stirring, the DMF was removed by evaporation under vacuum. The residue was taken in water (25 mL), dissolved by addition of aqueous sodium hydroxide solution 1M (pH 10) and subjected to dialysis using a SpectraPor 12-14 kDa membrane against water hydrochloric acid 50 mM (1 L volume; 2 changes over 24 h) and water (1 L). Lyophilization provided 4-hydroxybenzamide-PEI (1 g) at a modification degree of 13%. $^1$HNMR (D$_2$O) δppm: 3.8-2.45 (m, 4H, NHCH$_2$CH$_2$NH), 6.9 (m, 0.25H, CHaro), 7.18 (m, 0.25H, CHaro).

4-hydroxybenzamide-PEI (pBENPEI)

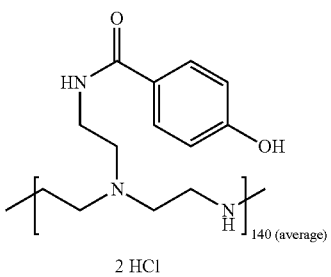

2 HCl

A solution of freshly prepared 4-hydroxybenzoic acid (635 mg; 4.6 mmol) and BOP (1.7 g; 5.06 mmol) in DMF (20 mL) was added dropwise and at room temperature to a solution of PEI (1 g, 23.2 mmol) in DMF (50 mL). After 2 hours under stirring, the DMF was removed by evaporation under reduced pressure. The crude product was taken in water, dissolved by addition of aqueous sodium hydroxide solution 1M (pH 11) and subjected to dialysis using a SpectraPor 12-14 kDa membrane against water (1 L, 2 changes over 24 h). Lyophilization provided 4-hydroxybenzamide-PEI (0.7 g) at a modification degree of 28%. $^1$H NMR (D$_2$O) δppm: 2.6 (bm, 2.9H, —NHCH$_2$CH$_2$NH—), 3.22 (m, 0.55H, PheCONHCH$_2$CH$_2$NH—), 3.35 (m, 0.55H, PheCONHCH$_2$CH$_2$NH) 6.57 (d, J=7.3 Hz, 0.55 H, CHaro), 6.97 (m, 0.55H, CHaro).

N-(4-aminophenyl), N'-PEI-thiourea (H2NPhePEI 15%)

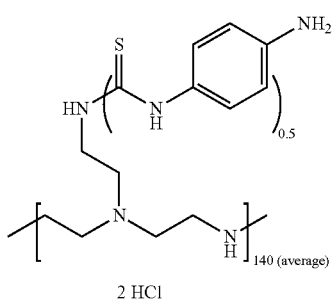

2 HCl

A solution of tert-butyl 4-isothiocyanatophenylcarbamate (500 mg; 2.02 mmol) in CH$_2$Cl$_2$ (50 mL) was added dropwise to a solution of PEI (580 mg; 13.5 mmol) in CH$_2$Cl$_2$ (40 mL). The reaction was completed in 30 min as judged by full consumption of the isothiocyanate. The solvent was then removed under reduced pressure and the residue was dissolved in aqueous HCl 3 M (30 mL). After 3 hours under stirring, the solution was carefully adjusted to pH 4.0 with aqueous NaOH 6 M. A dialysis, using a SpectraPor 12-14 kDa membrane against water (2 changes over 24 h) and freeze drying gave N-(4-aminophenyl), N'-PEI-thiourea (630 mg) as a yellow powder and at a 13% degree of modification. $^1$H NMR (D$_2$O) δppm: 4.02-2.65 (m, 3.7H, NHCH$_2$CH$_2$NH), 4.21 (m, 0.25H, CH$_2$NCS), 7.4-6.9 (2m, 0.5H, CHaro).

N-4-aminobenzyl, N'-PEI-thiourea (H2NPhePEI)

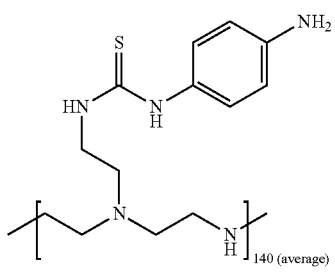

2 HCl

A solution of tert-butyl 4-isothiocyanatophenylcarbamate (500 mg; 2.02 mmol) in CH$_2$Cl$_2$ (50 mL) was added dropwise to a solution of PEI (265 mg; 6.16 mmol) in CH$_2$Cl$_2$ (40 mL). The reaction was then stirred for 30 min at room temperature and the solvent was removed by evaporation under reduced pressure. The residue was dissolved in aqueous HCl 3 M (30 mL) and the solution was carefully adjusted to pH 4.0 with aqueous NaOH 6 M. Dialysis (SpectraPor 12-14 kDa membrane) against water (2 changes over 24 h) and freeze dried provided N-(4-aminophenyl), N'-PEI-thiourea (650 mg) as a yellow powder. $^1$H NMR (D$_2$O) δppm: 4.0-2.67 (m, 3.3H, NHCH$_2$CH$_2$NH), 4.21 (m, 0.7H, CH$_2$NCS), 7.35 (bm, 1.4H, CHaro).

O-Benzyl Serine-PEI (BzlSPEI)

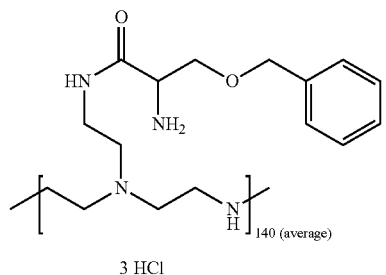

3 HCl

A solution of succinimidyl ester of N-Boc, O-Benzyl, Serine (5 g, 12.7 mmol) in DMF/CH$_2$Cl$_2$ 1/1 mixture (20 mL) was added at room temperature to a solution of polyethylenimine (1.4 g, 32 mmol in ethylenimine) in CH$_2$Cl$_2$ (5 mL). After 2 days stirring, the solvents were removed under reduced pressure and the residue was treated with trifluoracetic acid (20 mL) for 1 h at room temperature. The excess acid was coevaporated under reduced pressure twice with ethanol (50 mL). The residue was washed twice with diethylether (50 mL) and taken up in water (10 mL). After full dissolution, the solution was completed with aqueous 2M HCl (10 mL) and 5 M NaCl (2 mL). The milky solution was subjected to dialysis using a SpectraPor 12-14 kDa membrane against water (1 L, 5 changes over a 48 h period). Lyophilization afforded the product as a white powder. $^1$H NMR (D$_2$O) δppm: 2.4-3.7 (12.5H), 4.0-4.5 (m, 3H), 7.2-7.4 (m, 5H). $^{13}$C NMR (D$_2$O) δppm: 35.9, 45.8, 47.3, 49.3, 51.1, 53.1, 67.5, 73.5, 128.2, 128.4, 128.5, 128.8, 136.8, 167.6, 168.8.

Tyramine-O-acetamide-PEI 7

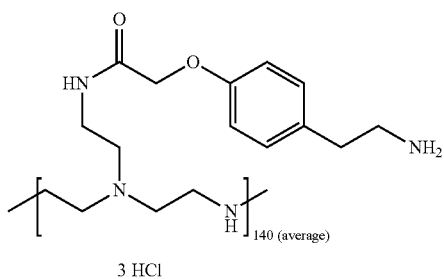

3 HCl

A solution of succinimidyl ester of N-Boc tyramine O-acetic acid (0.5 g, 1.1 mmol) in DMF/CH$_2$Cl$_2$ 1/1 mixture (4 mL) was added at room temperature to a solution of polyethylenimine (0.14 g, 3.2 mmol in ethylenimine) in CH$_2$Cl$_2$ (1 mL). After 2 days stirring, the solvents were removed under reduced pressure and the residue was treated with trifluoracetic acid (4 mL) for 1 h at room temperature. The excess acid was coevaporated under reduced pressure twice with ethanol (25 mL). The residue was washed twice with diethylether (10 mL) and taken up in water (5 mL). After full dissolution, the solution was completed with aqueous 2M HCl (2 mL). The solution was subjected to dialysis using a SpectraPor 12-14 kDa membrane against water (0.5 L, 5 changes over a 48 h period). Lyophilization afforded the product as a white powder. 1H NMR (D2O) δppm: 2.5-3.9 (15H), 4.1-4.5 (m, 2H), 6.8 (br, 2H), 7.1 (br, 2H). 13C NMR (D$_2$O) δppm: 31.9, 40.7, 43.8, 47.0, 50.0, 60.6, 115.1, 130.1, 130.2, 156.5, 172.4

Vanillamide-polyethylenimine (30%)

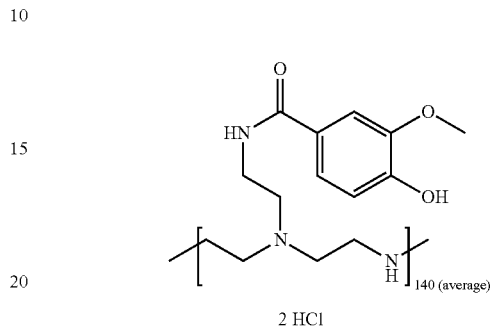

2 HCl

A solution of succinimidyl ester of vanillic acid (2.8 g, 10.5 mmol) in DMF (20 mL) was added at room temperature to a solution of polyethylenimine (0.9 g, 20.9 mmol in ethylenimine) in methanol (5 mL). After 2 days stirring, the residue was treated with NaOH 1M (5 mL) for 1 h at room temperature. The pH of the solution was then adjusted to pH 7.0 by addition of aqueous 0.5 M HCl and the solution was subjected to dialysis using a SpectraPor 12-14 kDa membrane against water (1 L, 5 changes over a 48 h period). Lyophilization afforded the product as yellow powder (1.4 g, 67% yield). $^1$H NMR (D$_2$O) δppm: 2.0-3.9 (16H), 6.6 (s br, 1H), 6.9-7.4 (m, 2H). $^{13}$C NMR (D$_2$O) δppm: 36.6, 49.9, 56.0, 115.0, 121.0, 146.9, 150.3. $\lambda_{max}$(ε calculated for ethylenime unit): 290 nm (2000 M$^{-1}$.cm$^{-1}$), 260 nm (4000 M$^{-1}$.cm$^{-1}$).

Vanillamide-oligoethylenimine (Vani-OEI)

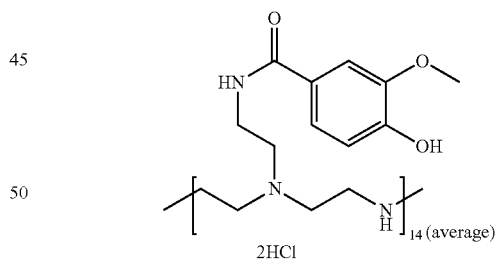

2HCl

A solution of succinimidyl ester of vanillic acid (1.4 g, 5.25 mmol) in DMF (10 mL) was added at room temperature to a solution of polyethylenimine 2000 Da (0.5 g, 11.6 mmol in ethylenimine) in methanol (5 mL). After 2 days stirring, the residue was treated with NaOH 1M (2 mL) for 1 h at room temperature. The pH of the solution was then adjusted to pH 7.0 by addition of aqueous 0.5 M HCl and the solution was subjected to dialysis using a SpectraPor 1000 Da membrane against water (1 L, 5 changes over a 48 h period). Lyophilization afforded the product as yellow powder (0.9 g, 75% yield). $^1$H NMR (D$_2$O) δppm: 2.4-3.9 (16H), 6.7 (s br, 1H), 6.9-7.4 (m, 2H). $\lambda X_{max}$(ε calculated for ethylenime unit): 290 nm (2000 M$^{-1}$.cm$^{-1}$), 260 nm (4000 M$^{-1}$.cm$^{-1}$).

2-hydroxybenzamide-polyethylenimine (SaliPEI)

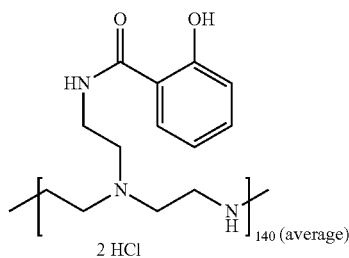

2 HCl

A solution of succinimidyl ester of salicylic acid (1.47 g, 6.2 mmol) in DMF (15 mL) was added at room temperature to a solution of polyethylenimine (0.9 g, 20.9 mmol in ethylenimine) in $CH_2Cl_2$ (3 mL). Two hours later, the reaction mixture was completed with methanol (20 mL) and stirred for 24 h. The solvents were removed under reduced pressure and the residue was treated with NaOH 1M (20 mL). The solution was subjected to dialysis using a SpectraPor 12-14 kDa membrane against water (1 L, 2 changes over a 24 h period), aqueous HCl (1 L, 6 changes over a 48 h period) and water (1 L, once for 6 h). Lyophilization afforded the product as a powder (1.8 g, 86% yield). $^1$H NMR ($D_2O$) δppm: 2.0-3.9 (13.2 H), 6.7-7.6 (m, 4H). $\lambda_{max}$(ε calculated for ethylenime unit): 300 nm (790 $M^{-1}.cm^{-1}$).

2-hydroxybenzamide-oligoethylenimine (Sali-OEI)

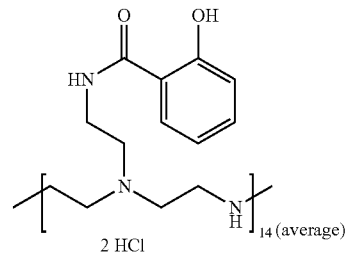

2 HCl

A solution of succinimidyl ester of salicylic acid (1.4 g, 5.9 mmol) in DMF (10 mL) was added at room temperature to a solution of polyethylenimine 2000 Da (0.9 g, 20.9 mmol in ethylenimine) in MeOH (40 mL). After 1 day stirring, the solution was subjected to dialysis using a SpectraPor 1000 Da membrane against water (1 L, 2 changes over a 24 h period), aqueous HCl 50 mM (1 L, 6 changes over a 48 h period) and water (1 L, once for 6 h). Lyophilization afforded the product as a yellow powder (1.2 g, 60% yield). $^1$H NMR ($D_2O$) δppm: 2.0-3.9 (13.2 H), 6.7-7.6 (m, 4H). $\lambda_{max}$(ε calculated for ethylenime unit): 300 nm (790 $M^{-1}.cm^{-1}$) $^{13}$C NMR ($D_2O$) δppm: 36.1, 44.7, 49.9, 117.1, 120.2, 134.5, 135.5.

4-hydroxyphenylacetamide-oligoethylenimine

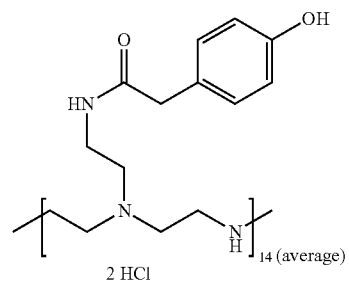

2 HCl

A solution of succinimidyl ester of 4-hydroxyphenylacetic acid (1.43 g, 5.74 mmol) in DMF (10 mL) was added at room temperature to a solution of polyethylenimine 2000 Da (0.817 g, 19 mmol in ethylenimine) in MeOH (40 mL). After 1 day stirring, the solution was subjected to dialysis using a SpectraPor 1000 Da membrane against water (1 L, 2 changes over a 24 h period), aqueous HCl 50 mM (1 L, 6 changes over a 48 h period) and water (1 L, once for 6 h). Lyophilization afforded the product as a yellow powder (1.2 g, 52% yield). $^1$H NMR ($D_2O$) δppm: 2.0-3.7 (16.6 H), 6.7 (s br, 2H), 6.9 (s br, 2H).

4-hydroxybenzamide-oligoethylenimine (pBEN-OEI)

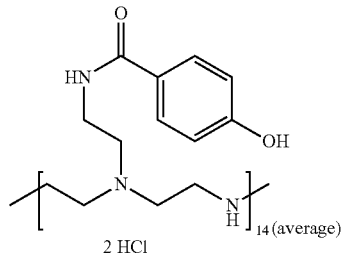

2 HCl

A solution of succinimidyl ester of 4-hydroxybenzoic acid (0.7 g, 2.95 mmol) in DMF (5 mL) was added at room temperature to a solution of polyethylenimine 2000 Da (0.45 g, 10.45 mmol in ethylenimine) in MeOH (15 mL). After 1 day stirring, the solution was subjected to dialysis using a SpectraPor 1000 Da membrane against water (1 L, 2 changes over a 24 h period), aqueous HCl 50 mM (1 L, 6 changes over a 48 h period) and water (1 L, once for 6 h). Lyophilization afforded the product as a yellow powder (0.8 g, 60% yield). $^1$H NMR ($D_2O$) δppm: 2.0-3.9 (13.2H), 6.7 (s, br, 2H), 7.5 (s, br, 2H). $\lambda_{max}$(ε calculated for ethylenime unit): 300 nm (790 $M^{-1}.cm^{-1}$).

Tyrosine-OEI

A solution of succinimidyl ester of N-Boc-Tyrosine (1.2 g, 3.1 mmol) in DMF (5 mL) was added at room temperature to a solution of polyethylenimine 1800 Da (0.33 g, 7.75 mmol in ethylenimine) in MeOH (10 mL). After 2 days stirring, solvents were removed under reduced pressure and the residue was treated with trifluoracetic acid (15 mL) for 1 h at room temperature. The excess acid was coevaporated under reduced pressure twice with ethanol (50 mL). The residue was washed twice with diethylether (50 mL) and taken up in water (10 mL). After full dissolution, the solution was completed with aqueous 2M HCl (10 mL) and subjected to dialysis using a SpectraPor 3500 Da membrane against water (1 L, 5 changes over a 48 h period). Lyophilization afforded the product (500 mg, 3.9 mmol in ethylenimine, 50%) as a white powder. $^1$H NMR ($D_2O$) δ 2.4-3.7 (13.3H), 4.1 (s broad, 1H), 6.8 (s broad, 2H), 7.1 (s broad, 2H). $\lambda_{max}$(ε calculated for ethylenime unit): 274 (466 $M^{-1}.cm^{-1}$).

Size Measurement

The apparent sizes were determined via dynamic light scattering measurements using a NanoZS apparatus (Malvern instruments, Paris, France) with the following specifications: sampling time=90 s; refractive index of medium=1.3402; refractive index of particles=1.47; medium viscosity=1.145 cP and temperature=25° C. Data were analyzed using the multimodal number distribution software included with the instrument.

Determination of polymer aggregation pH

Self aggregation was determined by turbidity. Each polymer (HCl salt) was first solubilized in water at a 20 mM concentration (0.5 mL volume). The stirred solution was then titrated by addition of NaOH solution (0.25 M, 1 µL increment) until occurrence of aggregate as seen by turbidity. pH of the solution was then measured with a calibrated pH meter. The turbid solution was then titrated with HCl (0.1 M, 1 µL increment) up to full dissolution and the pH measured again. For all polymer the transition was relatively narrow and within 0.2 pH unit.

Materials for the siRNA and Oligonucleotide Delivery Experiments

Cell culture media were supplemented with 10% FBS (Perbio, Brebières, France), 100 units/mL penicillin, 100 µg/mL streptomycin and 2 mM L-glutamine (Eurobio, Courtaboeuf, France). Cells were maintained at 37° C. in a 5% $CO_2$ humidified atmosphere. A549Luc cells (human lung carcinoma; CCL-185; ATCC) were transformed to stably express the Photinus pyralis luciferase gene originating from the pGL3 plasmid (Clontech, Mountain View, Calif.) and a resistance gene against G418. A549Luc cells were grown in RPMI 1640 medium. Hela705 are Hela cells that were stably transformed with a luciferase gene in which the coding region is interrupted by a mutated β-globin intron (Kang et al., 1998). Hela705 were grown in DMEM medium. Luciferase gene expression was determined 48 h after delivery with a commercial kit using manufacturer's protocol (Promega, Charbonnières, France). The luminescence was measured from 1 µL of lysate during is with a luminometer (Centro LB960 XS; Berthold, Thoiry, France). Luciferase activity was expressed as light units integrated over 10s (RLU) and normalized per mg of cell protein by using the BCA assay (Pierce, Brebières, France). The errors bars represent standard deviation derived from triplicate experiments. Efficiency was calculated relative to cells treated with the same and corresponding formulation but containing a non-specific oligonucleotide.

PAGE-purified oligonucleotides were purchased from Eurogentec (Seraing, Belgique) and stored at −20° C. as solution in RNase-free water. The luciferase gene originating from pGL3 plasmid was silenced with a RNA duplex of the sense sequence: 5'-CUU ACG CUG AGU ACU UCG A (SEQ ID NO: 1). Untargeted pGL2luc RNA duplex was of sequence 5'-CGU ACG CGG AAU ACU UCG A (SEQ ID NO: 2). The oligonucleotide, active for splicing interference, was a 2'-O-methyl-phosphorothioate of sequence 5'-CCU CUU ACC UCA GUU ACA (SEQ ID NO: 3). The control oligonucleotide was a 2'-O-methyl-phosphorothioate of sequence 5'-GGC CAA ACC UCG GCU UAC CU (SEQ ID NO: 4).

Determination of Polyplexes Stability 50 pmol of siRNA and 100 nmol of polymer buffered to pH 6.0 were prepared either in RPMI (15 µL, final pH of 7.8) or in water (15 µL, final pH of 6.0). Complexes were then incubated for 30 min with increasing charge excess of heparin (Sigma-Aldrich, Saint-Quentin-Fallavier, France). The mixture was then loaded onto a 2% agarose gel containing 1 mM EDTA and 40 mM Tris acetate buffer pH 8.0, and subjected to electrophoresis for 30 min at 90V. After staining with ethidium bromide solution (0.5 µg/mL) for 15 min, siRNA released from polyplexes by heparin were visualized with a UV transilluminator and quantified using a picture analysis software (NIH ImageJ).

Determination of the Polymer Toxicity (MTT Assay)

The MTT assay was performed in triplicate. A549luc or Hela705 cells were seeded into 96-well plates at a density of 5,000 cells per well (100 µL cell culture medium). 24 h later, the polymers (20 µL), at different concentrations, were added to obtain a final concentration as indicated in the graph. 24 h later, and to ensure optimal cell growth, each well was completed with an optional addition of cell medium containing serum (100 µL). 48 h after polymers addition, the cell culture medium was removed from each well and replaced with RPMI without serum (200 µL). (3-(4,5-dimethylthiazol-2-yl)-2,5-diphenyl tetrazolium bromide) (MTT, Invitrogen) solution in PBS (5 mg/mL, 20 µl) was then added to obtain a final concentration of 0.5 mg MTT/mL. After 4 h incubation at 37° C., excess reagent was removed by aspiration. The formazan crystals were dissolved in DMSO (100 µl) and measured spectrophotometrically in a microplate reader at a wavelength of 570 nm. The relative cell viability of treated cells was calculated compared to untreated cells.

SiRNA Delivery Experiments

The day before experiments, A549Luc cells were platted at 25 000 cells per well in 24-well plates. Typically, an aqueous solution of the polymer-HCl salt (10 mM in ethylenimine) (24 nmol, 1.2 µL) was added to RPMI medium without serum (50 µL). After 10 min, the polymer solution (50 µL) was added to a solution of siRNA (6 pmol, 88 ng) in RPMI medium (50 µL). After agitation, the complexes were incubated for 30 minutes at room temperature and added into a well by dilution with the cell medium containing serum (0.5 mL). 24 h later, and to ensure optimal cell growth, each well was completed with an optional addition of cell medium containing serum (0.5 mL). The gene expression profile was analyzed 48 h after addition of the complexes.

Delivery of Oligonucleotide for Interference with mRNA Splicing Mechanism

The day before experiments, Hela705 cells were platted at 50000 cells per well in 24-well plates. First procedure (for mimicking in vivo administration): Polymer stock solutions in water were adjusted to 6.0 with 1M NaOH and prepared at a 150 mM concentration. Typically, a 15 µL-aqueous 4.5% glucose solution containing each polymer (630 nmol in ethylenimine) was rapidly mixed with a 15 µL-aqueous 4.5% glucose solution containing the oligonucleotide (20 µg, 3.3 nmol or 63 nmol of phosphorothioate). After 15 min incubation, aliquots were withdrawn and added to the cell by direct dilution within the cell culture medium containing serum. Second procedure: Polymers were at 10 mM stock concentration. Polymer to oligonucleotide ratio as well as quantity of oligonucleotide was varied accordingly. Typically, the oligonucleotide (0.4 µg, 66 pmol or 1.25 nmol of phosphrothioate) in RMPI without serum (100 µL) was added rapidly to the polymer (1.25 µL; 12.5 nmol). After 15 min incubation, the complexes were added to the cells by direct dilution within the cell culture medium containing serum (1 mL).

Results and Discussion

Synthesis of the Polymers

Figure 2:
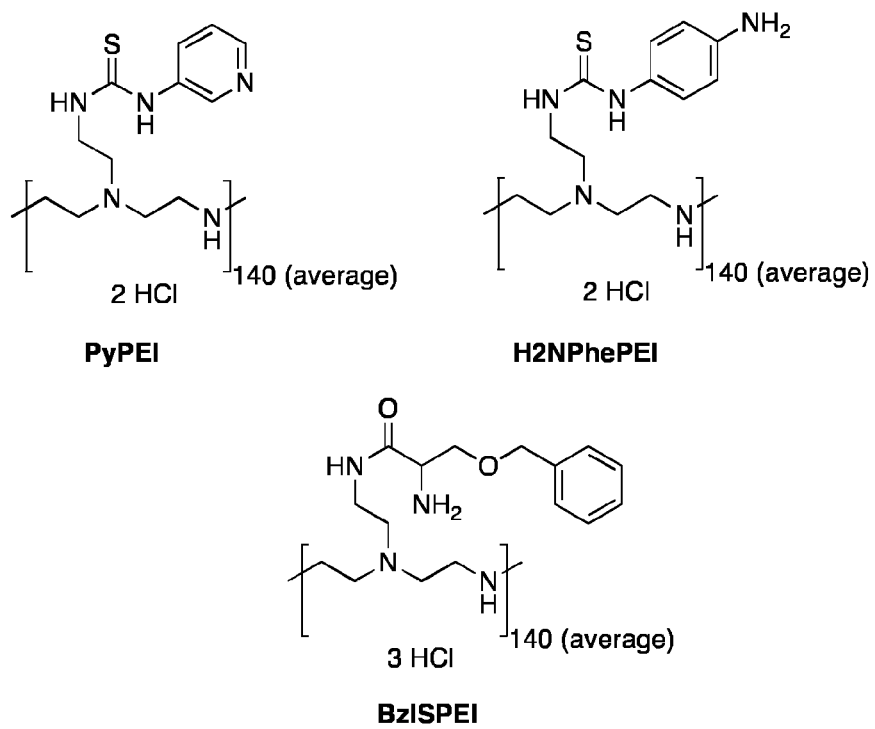
FIG. 2: Chemical structure of the aromatic polyethylenimines containing a thiourea bond and of the Benzyl-modified serine-PEI.
Figure 3:
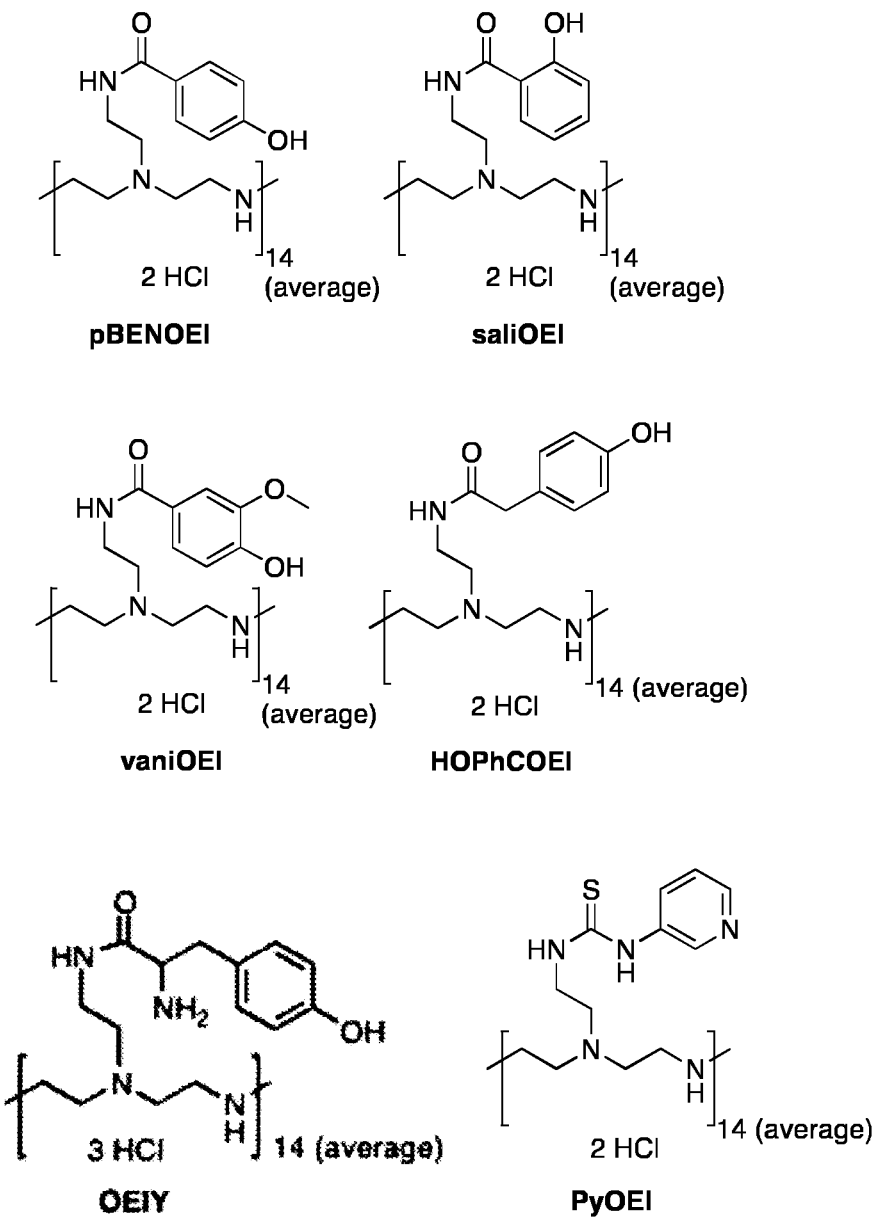
FIG. 3: Chemical structure of the different aromatic modified oligoethylenimine.

Aliphatic amines of commercially available PEIs of 25000 Da (abbreviated as PEI) were first modified at a 30% extend (relative to ethylenimine unit) by standards chemical procedures in organic solvents (see description in Materials and Methods) to different aromatic groups via an amide bond (FIG. 1) or via a thiourea bond (FIG. 2). The inventors also prepared a benzyl-serine-PEI conjugate (FIG. 2) and similar aromatic-oligoethylenimine polymers (FIG. 3) but starting from a polyethylenimine of low molecular weight (noted as OEI, MW average of 1800 Da). As controls, tyrosine-modified PEIs (noted as PEIY and OEIY for polymers deriving from 25 kDa and 1800 Da PEI, respectively) were also prepared as previously described (Creusat and Zuber, 2008). Finally, some polymers were also prepared as a lower degree of modification of 15% as noted. Yields were typically in the 50-80% range after purification by dialysis. $^1$H NMR integration of characteristic peaks confirmed the various extend of PEI modification.

Aggregation Properties of the Polymers as a Function of the pH.

Figure 4:
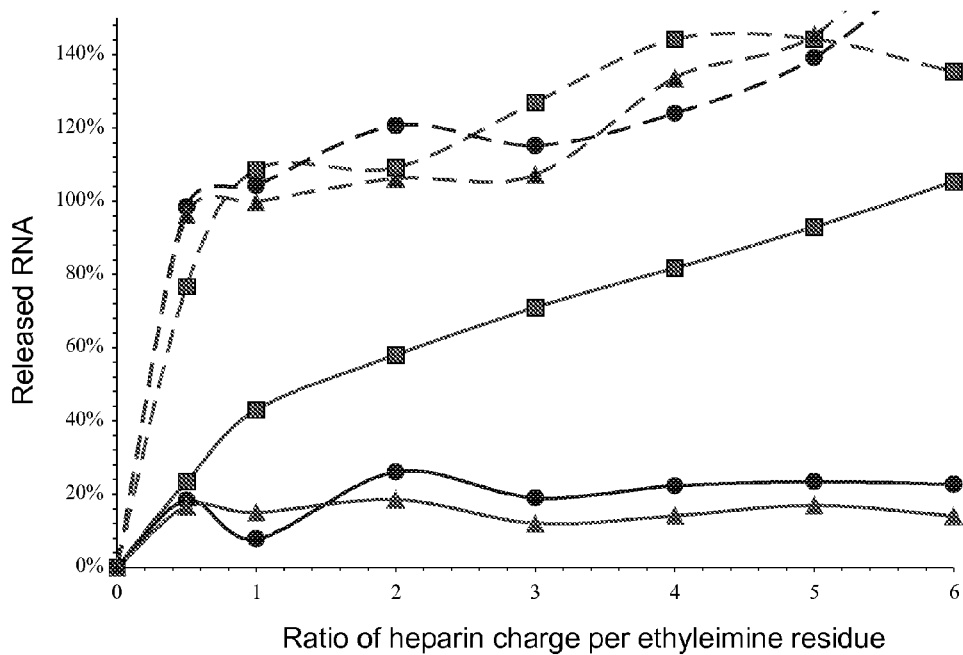
FIG. 4: Evaluation of the electrostatic stability of the siRNA polyplexes. Polyplexes (N/P 50, made with 0.7 μg siRNA and either PyPEI (square), OEIY (dot) or pBENOEI (triangle) were incubated for 30 min with increasing amounts of heparin in RPMI medium (full lines) or at pH 6.0 (dotted lines) and release of siRNA was determined from agarose gel electrophoresis analyses.

As hydrochloride salts, all polymers are soluble in water and can be stored in solution for extensive periods at 0-4° C. or at −20° C. However, PEIs exist in a wide variety of protonation states, which can affect their solvation in aqueous media especially following chemical modification of the PEI backbone. Aggregation ability of the different polymers may therefore vary according to pH and ionic forces of the solution. Indeed, while PEI or OEI remained soluble, PEIY, vaniPEI, saliPEI, pBENPEI and PyPEI, OEIY, SaliOEI, and pBENOEI self-aggregated in an aqueous medium compatible with cell physiology such as the RMPI cell growth medium (Table 1 and Table 2 presented below). In the next experiment, the inventors determined precisely the pH value where aggregation occurs. Each polymer-HCl salt (20 mM) was carefully deprotonated with NaOH until turbidity and the pH value was measured (Table 1 and Table 2 presented below). Results show that the different chemical modifications confer to polyethylenimines of variable molecular weights (PEI or OEI) aggregating properties at various pHs (pHs in the 5.0 to 8.0 range) that are compatible to cell physiology. The polymers self-aggregate in extracellular alkaline liquids but disassemble in slight acidic conditions that might be encountered in endosomes.

membranes of adherent cells to enter into cells. While polyanions may effectively displace siRNA from polyplexes in extracellular environments, the inventors investigated the stability of the siRNA polyplexes in presence of heparin, a natural polymer with a high anionic density in a cell culture medium pH 7.8. Yet, for effectiveness, siRNA should be released from the polyplexes and this can occur at acidic pH encountered in endosomes buffered with PEI. The stability of the polyplexes was therefore also investigated at pH 6.0 (Akinc et al., 2005; Sonawane et al., 2003). siRNA polyplexes were prepared in RPMI medium (pH 7.8) or at pH 6.0 at a N/P ratio of 50 to ensure full complexation and then incubated for 30 min with increasing quantities of heparin. The mixtures were then subjected to analysis by agarose gel electrophoresis. Release of siRNA was monitored after ethidium bromide staining and quantified (FIG. 4). At pH 7.8, heparin effectively displaces PEI from the weakly cohesive siRNA/PEI complexes and provokes a quantitative liberation of siRNA, even at a low heparin to ethylenimine ratio. According to the working hypothesis, transformation of the soluble PEI into cohesive species does indeed allow the stabilization of the polyplexes against electrostatic displacement, but in various extents. PyPEI forms moderately stable complexes while OEIY and pBENOEI appear to form complexes that offer a superior resistance to electrostatic displacement. On the other hand, acidity compatible to endosomes provokes a full release of the siRNA from the polyplexes made with the now soluble polymers.

Cytotoxicity

Figure 5:
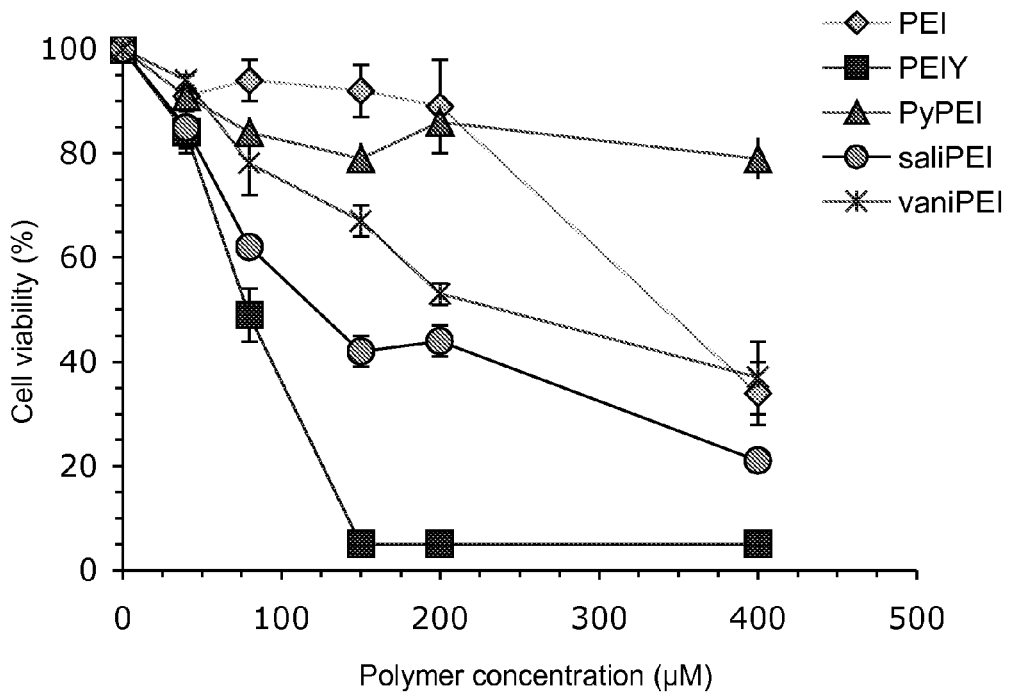
FIG. 5: Estimation of Hela cell viability in the presence of increasing concentrations of various PEIs, as indicated. Cell viability was estimated by measuring the redox activity of living cells using the 3-(4,5-Dimethylthiazol-2-yl)-2,5-diphenyltetrazolium bromide (MTT) reduction assay.
Figure 6:
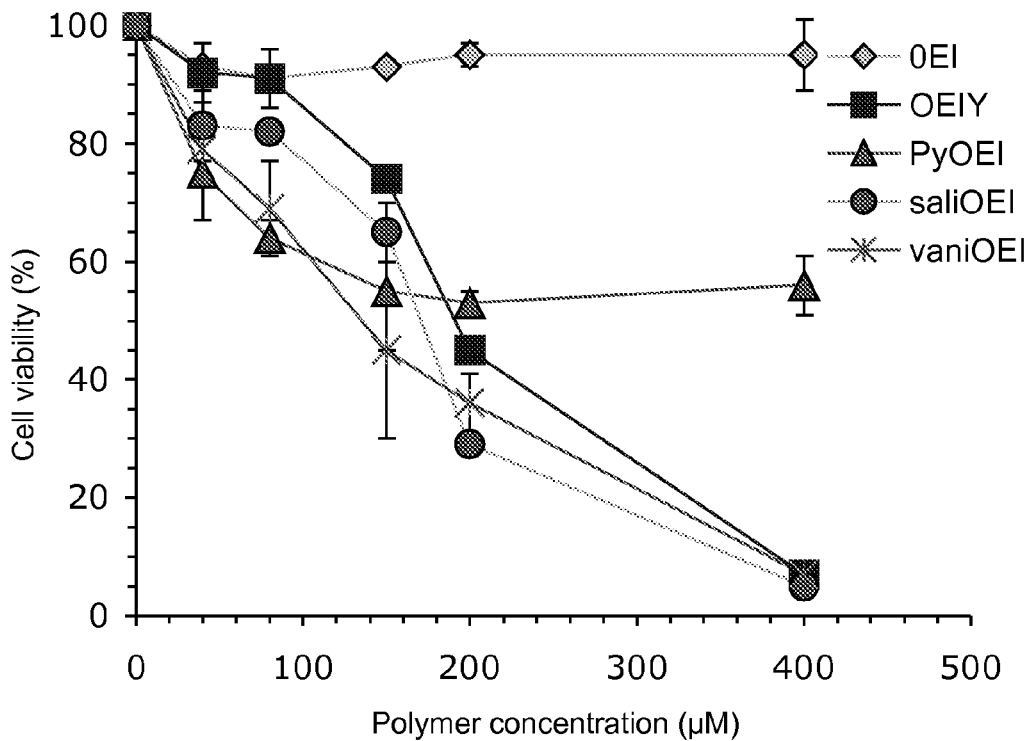
FIG. 6: Estimation of Hela cell viability in the presence of increasing concentrations of various OEIs, as indicated. Cell viability was estimated by measuring the redox activity of living cells using the 3-(4,5-Dimethylthiazol-2-yl)-2,5-diphenyltetrazolium bromide (MTT) reduction assay.
Figure 7:
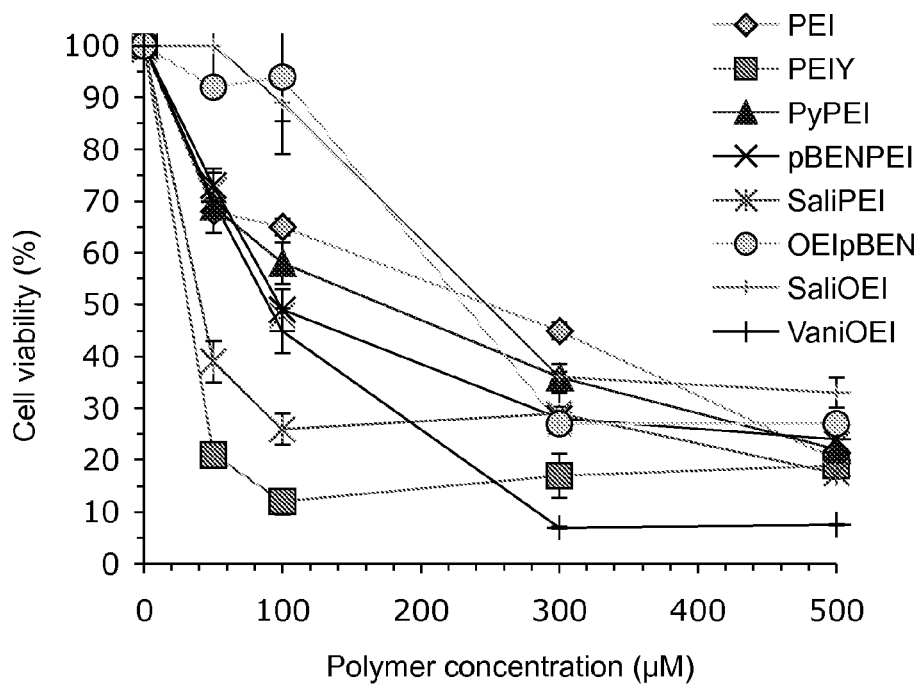
FIG. 7: Estimation of A5491uc cell viability in the presence of increasing concentrations of various OEIs, as indicated. Cell viability was estimated by measuring the redox activity of living cells using the 3-(4,5-Dimethylthiazol-2-yl)-2,5-diphenyltetrazolium bromide (MTT) reduction assay.

Cytotoxicity can be a limiting factor for the development of any drug carrier and, thus, is crucial to be considered at early stages. The effect of the different polymers on two different cell lines (Hela and A549luc) were therefore analyzed by measuring the cellular mitochondrial activity using the classical MTT assay (FIGS. 5, 6 and 7). Overall, the results indicated that the novel polymers, and in particular the PyPEI and the modified OEIs, perturb the cell physiology to a less extend than PEIY.

TABLE 1

Self-aggregation abilities of polyethylenimines as function of pH.

| Polymer | PEI | PEIY | vaniPEI | saliPEI | pBENPEI | PEIpy |
|---|---|---|---|---|---|---|
| Aggregation pH$^a$ | —$^b$ | 6.3 | 6.1 | 6.1 | 6.4 | 8.0$^c$ |
| Sizes of the polymer self-aggregates (nm)$^d$ | —$^e$ | 325 ± 28 | 514 ± 9 | 299 ± 12 | 377 ± 16 | 293 ± 52 |

$^a$corresponds to the pH for which polymer goes from a soluble to an aggregated state. The value was estimated by turbidity upon titration of a 20 mM polymer-HCl solution with NaOH.
$^b$fully soluble up to pH 9.0.
$^c$solution contained 150 mM NaCl. For this polymer, the turbidity might not be a good criteria since self-aggregates can be detected at pH 7.8
$^d$estimated in RPMI media, pH 7.8 from DLS data with 120 μM of the polymer.
$^e$No DLS signal detected. [e]

TABLE 2

Self-aggregation abilities of oligoethylenimines as function of pH.

| Polymer | OEI | OEIY | vaniOEI | saliOEI | pBENOEI | HOPheCH$_2$OEI |
|---|---|---|---|---|---|---|
| Aggregation pH$^a$ | —$^b$ | 7.6 | 6.3 | 6.5 | 6.4 | 7.3 |
| Sizes of the polymer self-aggregates (nm)$^d$ | —$^e$ | 452 ± 10 | 503 ± 17 | 362 ± 49 | 412 ± 12 | 410 ± 10 |

$^a$corresponds to the pH for which polymer goes from a soluble to an aggregated state. The value was estimated by turbidity upon titration of a 20 mM polymer-HCl solution with NaOH.
$^b$fully soluble up to pH 9.0.
$^c$solution contained 150 mM NaCl.
$^d$estimated in RPMI media, pH 7.8 from DLS data with 240 μM of the polymer.
$^e$No DLS signal detected. [e]

Figure 8:
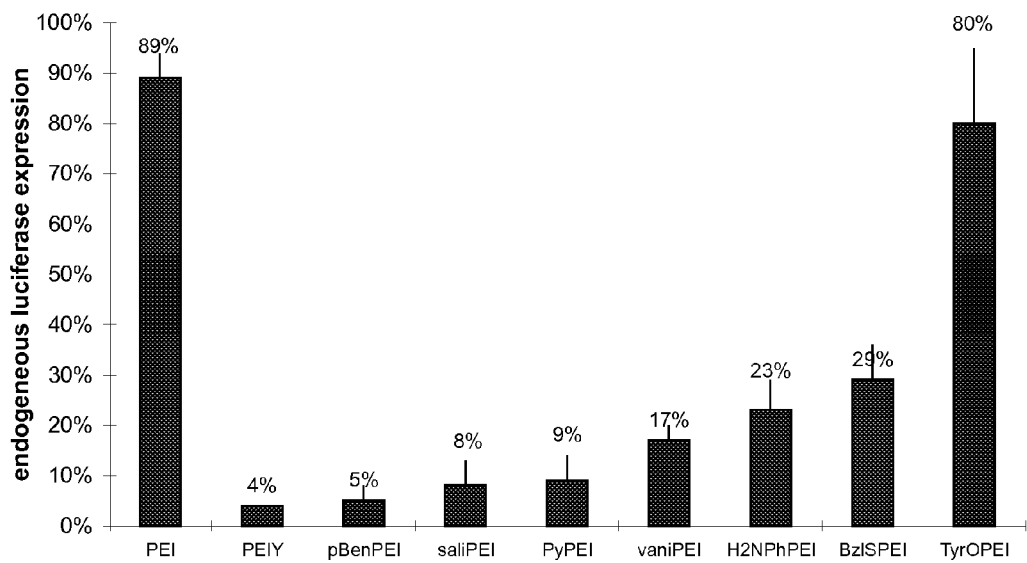
FIG. 8: Evaluation of the various polymer efficiency to deliver siRNA in mammalian cells. Luciferase-Targeting siRNA (6 pmol, 88 ng) were formulated with the indicated polymer (12 nmol) in RPMI and added to about 25,000 A5491uc cells which were stably transformed to express an endogeneous luciferase gene. Luciferase gene expression was measured 48 h and efficiency of the overall gene silencing process was relative cells treated with the same formulation but containing an untargeting siRNA.

Evaluation of siRNA/PEIY Polyplexes Stability in Extracellular Media and Ability to Release siRNA at Endosomal pHs Most synthetic delivery systems use initial electrostatic anchorage to sulfated (polyanionic) proteoglycans present on The results indicated that PyPEI and the modified OEIs offers an improved toxicological profile relative to PEIY siRNA Delivery Ability As previously indicated, siRNA duplexes can effectively and selectively silence the expression of a gene if the duplexes can be transferred into the cell. The property of the polymers to convey siRNA was evaluated using the firefly pGL3 luciferase gene as the targeted reporter. To avoid experimental bias generated by transient plasmid transfection, we used A549 cells that stably express the pGL3 gene. One of the most efficient routes for entry of synthetic delivery systems into endosomes uses initial electrostatic anchorage to sulfated proteoglycans present on cell membranes. One necessary condition for its employment is to build cationic particles. Particles were thus prepared by mixing excess of the polymer (12 nmol in ethylenimine) with siRNA (6 pmol) in RPMI (100 μL). The resulting assemblies then were simply added to cells (grown in presence of serum) to reach a final siRNA concentration of 10 nM. 48 h later, cells were lysed and the efficacy of the polymers were compared to that of PEIY, an already described siRNA delivery agent (FIG. 8). Results showed that pBENPEI, saliPEI, PyPEI, vaniPEI, H2NPhPEI and BzlSPEI (each modified at a 30% relative to ethylenimine residue) enable significant translocation of siRNA in the cell cytosol. Important to note, PEIY, pBENPEI, saliPEI and PyPEI cannot be statistically discriminated (in term of delivery efficiency) from each other.

Figure 9:
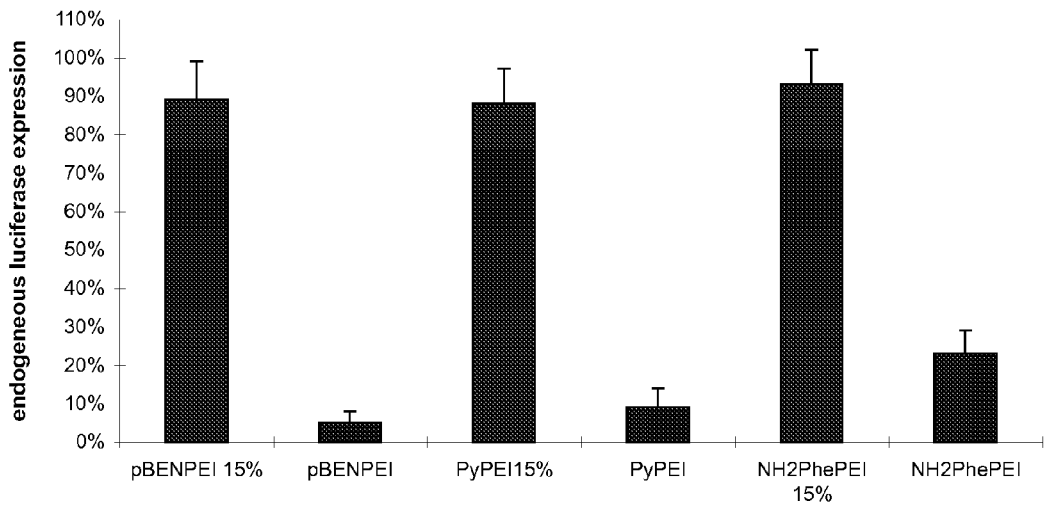
FIG. 9: Effect of the degree of modification of representative polymers on their siRNA delivery efficiencies. Luciferase-Targeting siRNA (6 pmol, 88 ng) were formulated with the indicated polymer (12 nmol) in RPMI and added to about 25,000 A5491uc cells which were stably transformed to express an endogeneous luciferase gene. Luciferase gene expression was measured 48 h and efficiency of the overall gene silencing process was relative cells treated with the same formulation but containing an untargeting siRNA.
Figure 10:
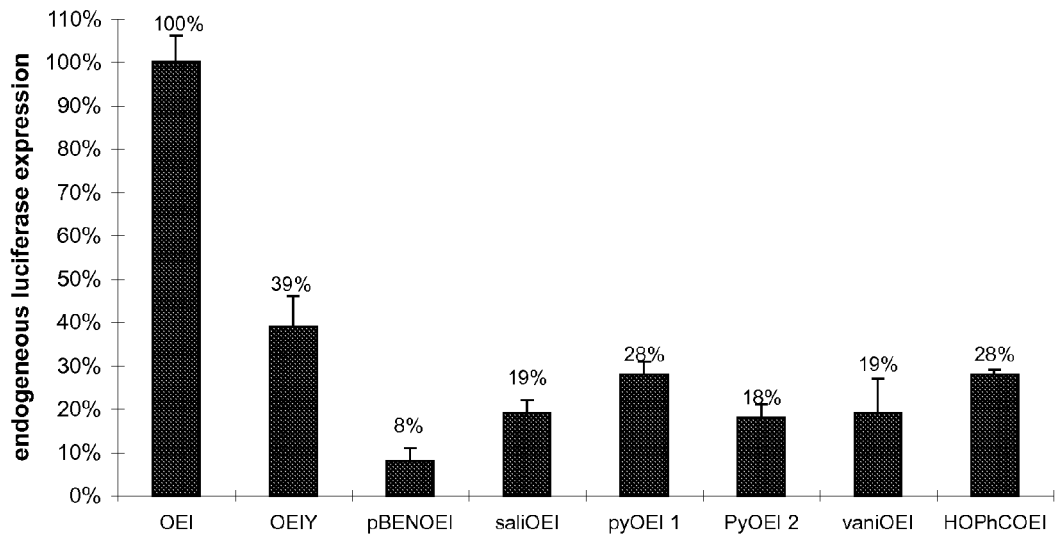
FIG. 10: Evaluation of the various polymer efficiency to deliver siRNA in mammalian cells. Luciferase-Targeting siRNA (6 pmol, 88 ng) were formulated with the indicated polymer (24 nmol) in RPMI and added to about 25,000 A5491uc cells which were stably transformed to express an endogeneous luciferase gene. Luciferase gene expression was measured 48 h and efficiency of the overall gene silencing process was relative cells treated with the same formulation but containing an untargeting siRNA.
Figure 11:
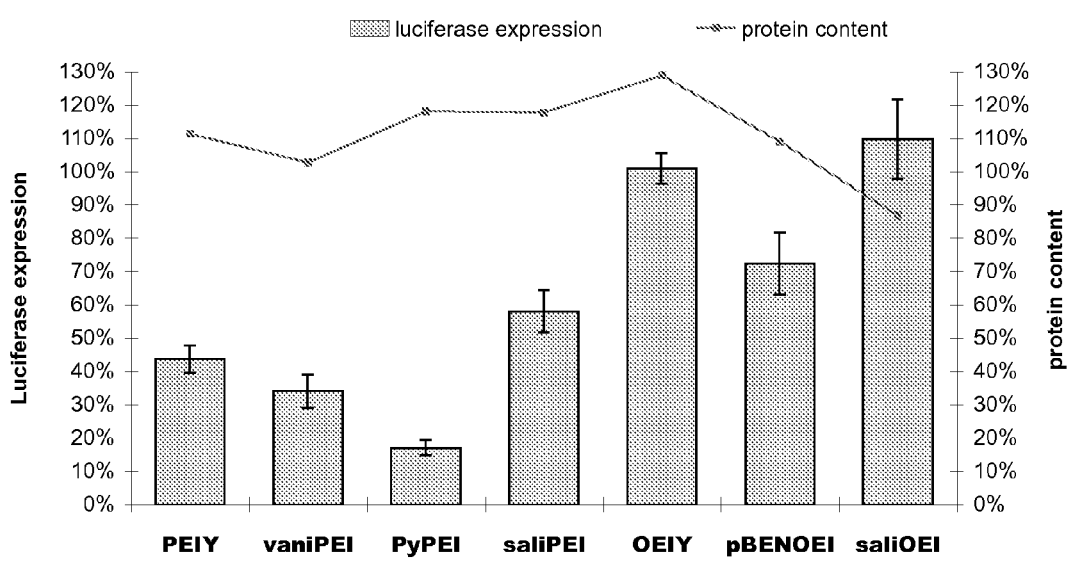
FIG. 11: Evaluation of the various polymer efficiency to deliver siRNA in mammalian cells (U87-EGFPLuc). Luciferase-Targeting siRNA (6 pmol, 88 ng) were formulated with the indicated polymer (24 nmol) in RPMI and added to about 25,000 U87egfpluc cells which were stably transformed to express an endogeneous luciferase-egfp gene. Luciferase gene expression was measured 48 h and efficiency of the overall gene silencing process was relative cells treated with the same formulation but containing an untargeting siRNA.

FIG. 9 shows that a 30% degree of modification of the polymer leads to better RNA delivery than a 15%. FIG. 10 shows that polymers of low molecular weights are also able to assist siRNA delivery into cells and actually to a better efficiency than the tyrosine-modified OEI. FIG. 11 shows that the various polymers can assist siRNA delivery to another cell line (U87egfpluc). In this experiment, the PyPEI appears a better than PEIY.

Figure 12:
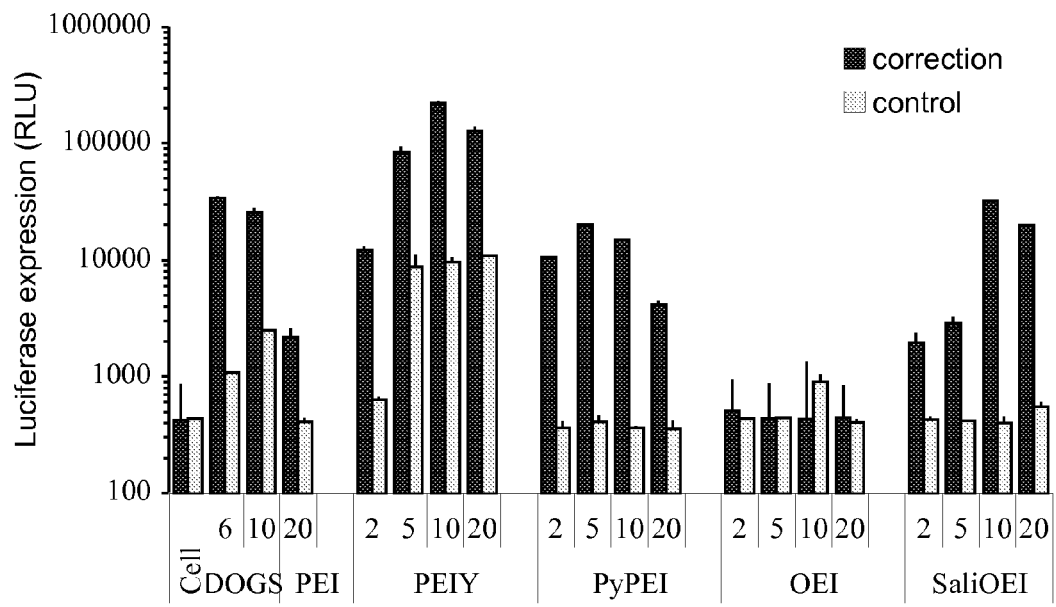
FIG. 12: Efficiency of the various formulations for delivering a splice correcting oligonucleotide in mammalian cells (Hela705). Levels of splice correction by ASO in formulation with the various polymers at the indicated N/P ratio, either with a correcting ASO (black bar) or with the control one (white bar). Formulations were prepared according to the second procedure (diluted conditions). The final concentration of polymers was of 20 µM. For N/P 2, 5, 10, 20, the concentrations of the ASO were of 520, 208, 104, 52 nM respectively. Luciferase activity, and hence splice correction, was quantified in relative luminescence units (RLU) and is shown as the raw amount detected per well. Each bar represents a mean±S.D. of two independent experiments.
Figure 13:
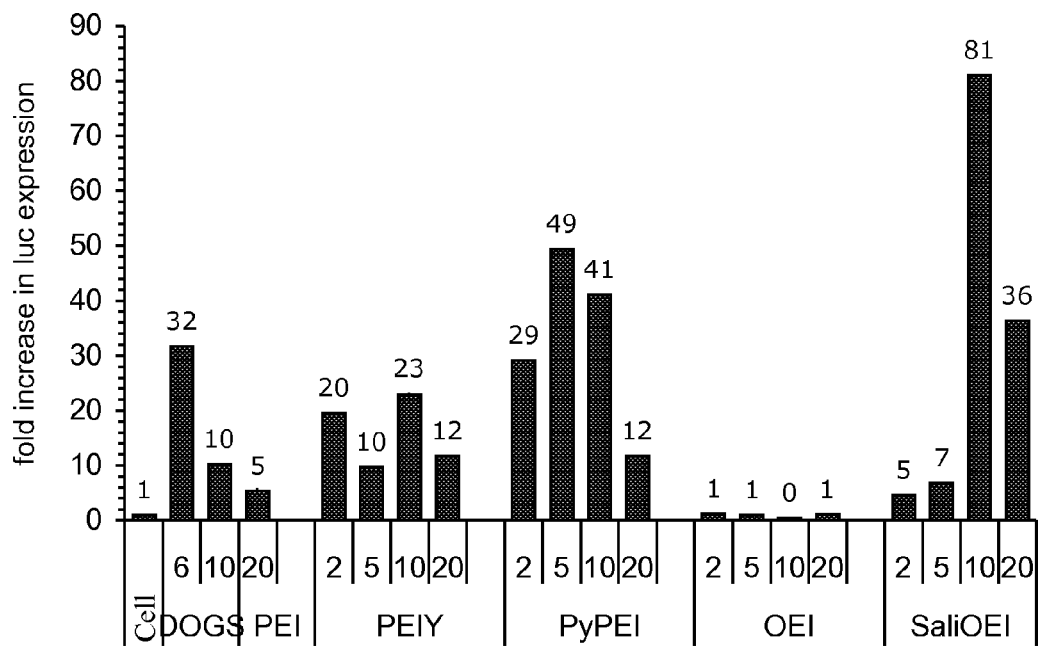
FIG. 13: Efficacy of the various formulations for delivering of a splice correcting oligonucleotide. Correction activity is shown as fold-increase in RLU relative to Hela705 cells that were treated with the same formulation but containing an uncorrecting ASO. Formulations were prepared according to the second procedure (diluted conditions). The final concentration for each polymer was of 20 µM. Concentration of ASO was decreased according to the indicated N/P ratio.

Evaluation of the Polymers to Deliver a Highly Modified Oligonucleotide for Interference with the mRNA Maturation Mechanism Hela 705 are cells stably transfected with a luciferase gene in which the coding region is interrupted by a mutated μ-globin intron (Kang et al., 1998). The mutation results in the activation of a cryptic splice site, which results in a defect splicing and a dysfunctional protein. Blocking of the mutation with a highly modified 2'-O-methyl-phosphorothioate antisens oligonucleotide (ASO) results in a correction of the splicing and, thus, the translated mRNA will correspond to the active form of the luciferase protein (Kang et al., 1998). To study the efficiency of the polymers to deliver ASOs, the inventors applied ASO/polymers complexes using a constant final concentration of 20 μM of polymer and variable amount of oligonucleotide. FIG. 12 shows that DOGS (Dioctadecylamidoglycyl Spermine), PEIY, PyPEI and saliOEI effectively deliver ASO in cells as monitored by the increase in luciferase activity of the correcting ASO (black bar). Interestingly to note, DOGS and PEIY seem to have an impact on their own on the splicing mechanism as seen by the undesired increase in luc activity using an uncorrecting ASO (white bars). Correction of this aberrant effect is done on the FIG. 13 by plotting correction activity as fold-increase in RLU relative to Hela705 cells that were treated with the same formulation but containing an uncorrecting ASO. In this way, saliOEI appears as a very promising agent to deliver modified ASO for interference with mRNA maturation mechanism.

Figure 14:
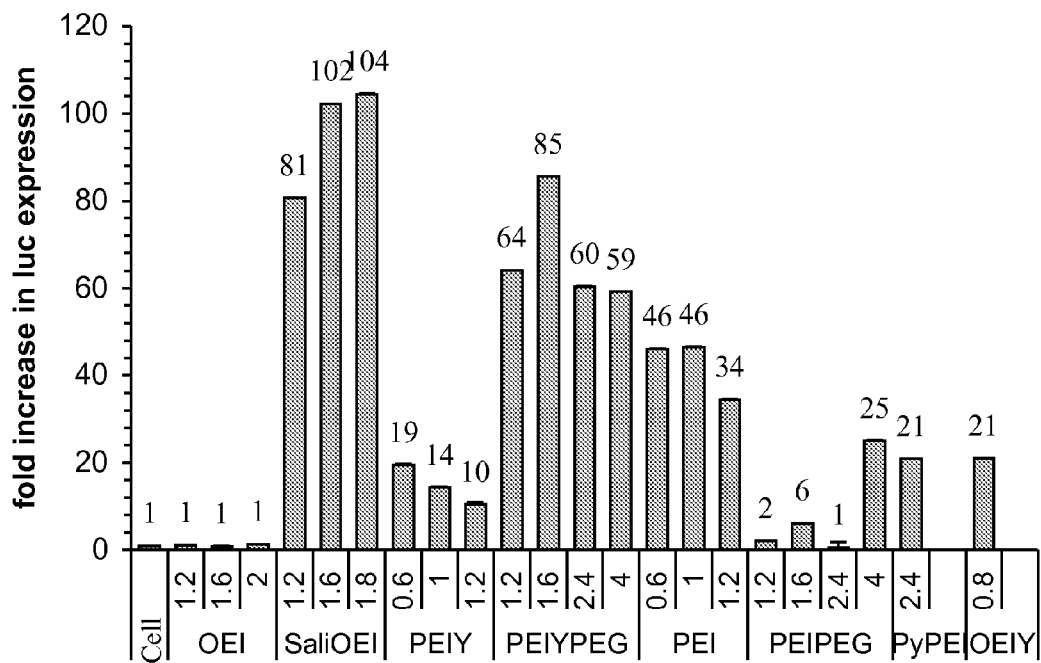
FIG. 14: Efficacy of the various formulations for delivering of a splice correcting oligonucleotide. Correction activity is shown as fold-increase in RLU relative to Hela705 cells that were treated with the same formulation but containing an uncorrecting ASO. Formulations were prepared according to the first procedure (concentrated conditions) to mimic in vivo administration. N/P ratios were of 10 and formulations were prepared in 4.5% glucose solution.
Figure 15:
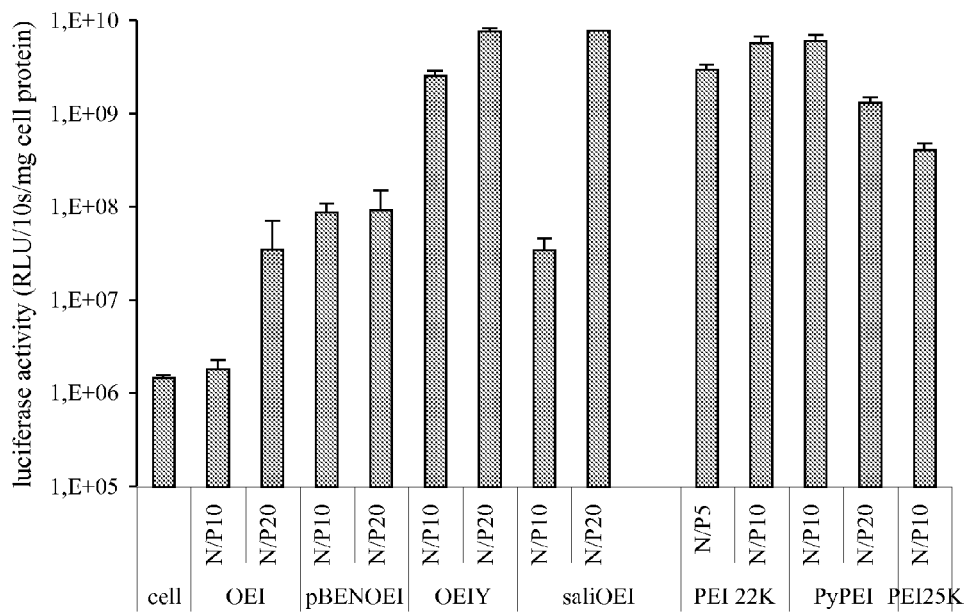
FIG. 15: Gene delivery experiments. pCMVluc (1 µg) was complexed with the indicated polymer at the indicated N/P value in RPMI medium (100 µL) and added to BHK cells grown in cell culture medium containing 10% FBS. Luciferase expression was monitored 24 h later.

Next, formulation and compositions of the formulations were optimized for in vivo administration. Indeed, in vivo administration needs concentrated solutions which can impact dramatically the sizes (and hence efficiency) of the delivery systems. Concentrated formulations (containing 0.66 μg of the oligonucleotide, N/P 10) were thus prepared in glucose solution and added to Hela705 cells for ASO-mediated exon-skipping. FIG. 14 shows saliOEI and PEIYPEG (PEIY modified with a PEG of MW 5000 at about 1%) to be also effective ASO delivery agents Gene Delivery Activity FIG. 15 shows that the various polymers (and in particular PyPEI and saliOEI) are also effective gene transfection agents.

CONCLUSION

In here, the inventors showed that they can prepare novel polymers that are effective in oligonucleotide delivery but also in gene delivery in cells. PyPEI and most OEI appears to offer also an improved toxicology profile (relative to PEIY) with comparable, sometimes better, efficiency. Interestingly to note, the hydroxyl group of serine-modified PEI (and related polymers) offer an interesting scaffold for further modification and can be easily used for conjugation to hydrophobic domains.

Example 2

Materials and Methods

Materials 3-(4,5-dimethylthiazol-2-yl)-2,5-diphenyl tetrazolium bromide (MTT) was purchased from Invitrogen. Branched PEI 25 kDa (40,872-7, batch 09529KD-466) and the other chemicals were purchased from Sigma-Aldrich (St Quentin, France) and were used as supplied. Water was deionized on a Millipore Milli-Q apparatus. Before use, regenerated cellulose dialysis membranes (SpectraPor 4, 12-14 kD, Spectrum-Labs) were soaked in MilliQ water (200 mL, 3 times, 8 h each) to remove preservatives. Chemical synthesis and work-ups were performed under a chemical fume hood and plastic tubes were guaranteed RNAse-free by the manufacturers. Experiments involving cell lines were performed according to the biosafety level 2 guidance. Animal experimentation was conducted according to French regulations. Buffer and water were sterilized by filtration through 0.22 μm pore membrane. The polymers and siRNA solutions were prepared using sterile media. All solutions were kept sterile by working under a class II microbiological safety cabinet. UV/Vis analysis was performed on a Shimadzu UV2401PC spectrometer. NMR spectra were performed on a Bruker DPX 400 MHz spectrometer. The modification degree of the polymer was determined relative to ethylenimine residues by integration of $^1$H NMR signals and was of 30+/−5% for all polymer otherwise indicated.

Succinimidyl Ester of Vanillic Acid

A solution of N,N'-Dicyclohexylcarbodiimide (20 g, 97 mmol) in $CH_2Cl_2$ (25 mL) was added dropwise and at 0-4° C. to a solution of N-hydroxysuccinimide (8.9 g, 77 mmol) and vanillic acid (11.8 g, 70 mmol) in ethylacetate (80 mL)/DMF (20 mL). The reaction mixture was then stirred overnight at room temperature. The dicyclohexylurea (DCU) was removed by filtration, washed with ethyl acetate (100 mL) and the combined organic phase was washed with saturated NaCl (100 mL), saturated $NaHCO_3$ (twice 100 mL), saturated NaCl (100 mL) and then dried over $MgSO_4$. The solvent was then removed under reduced pressure to give the product as a yellow solid (16.5 g; 70% yield). $^1$H NMR ($CDCl_3$) δppm: 2.9 (s, 4H), 3.9 (s, 3H), 6.9 (d, J=8.4 Hz, 1H), 7.55 (d, J=2.0 Hz, 1H, 7.75 (dd, J=2.0 Hz, J=8.4 Hz, 1H), 8.0 (s, 1H). $^{13}$C NMR (CDCl$_3$) δppm: 25.7, 56.2, 112.4, 114.8, 116.5, 125.9, 146.7, 152.2, 161.5, 169.5. ES-MS: (M calculated for C$_{12}$H$_{11}$N$_6$: 265.057) found: 288.049 ([MNa]$^+$).

Succinimidyl Ester of Salicylic Acid

A solution of N,N'-Dicyclohexylcarbodiimide (10.9 g, 53 mmol) in CH$_2$Cl$_2$ (5 mL) was added dropwise and at 0-4° C. to a solution of N-hydroxysuccinimide (6.19 g, 53.8 mmol) and salicylic acid (6.16 g, 44.7 mmol) in DMF (30 mL). The reaction mixture was then stirred overnight at room temperature and the dicyclohexylurea was removed by filtration and washed with ethyl acetate (200 mL). The combined organic phase was washed with saturated NaHCO$_3$ (twice 200 mL), citric acid 5% (200 mL), saturated NaCl (200 mL), dried over MgSO$_4$ and the solvent was removed under reduced pressure to give the product as a yellow solid (10.1 g, 95% yield). $^1$H NMR (CDCl$_3$) δppm: 2.9 (s, 4H), 6.95 (t, J=7.2 Hz, 1H), 7.05 (d, J=8.0 Hz, 1H), 7.58 (td, J=7.2 Hz, J=1.6 Hz, 1H), 8.0 (dd, J=8.0 Hz, J=1.6 Hz, 1H). $^{13}$C NMR (CDCl$_3$) δppm: 25.6, 108.1, 118.0, 120.0, 130.1, 137.9, 161.9, 165.0, 169.1. ES-MS: (M calculated for C$_{11}$H$_9$NO$_5$: 235.048) found: 258.038 ([MNa]$^+$).

Succinimidyl Ester of Nicotinic Acid

A solution of N,N'-Dicyclohexylcarbodiimide (7.0 g, 33.98 mmol) in CH$_2$Cl$_2$ (10 mL) was added dropwise and at 0-4° C. to a solution of N-hydroxysuccinimide (4.1 g, 35.6 mmol) and nicotinic acid acid (3.89 g, 31.6 mmol) in DMF (30 mL). The reaction mixture was then stirred overnight at room temperature and the dicyclohexylurea was removed by filtration and washed with ethyl acetate (200 mL). The combined organic phase was washed with saturated NaHCO$_3$ (twice 200 mL), citric acid 5% (200 mL), saturated NaCl (200 mL), dried over MgSO$_4$ and the solvent was removed under reduced pressure to give the product as a white solid (5.7 g, 80% yield). $^1$H NMR (CDCl$_3$) δppm: 2.8 (s, 4H), 7.2-7.43 (m, 1H), 8.31-8.35 (m, 1H), 8.82-8.84 (m, 1H), 9.26 (d, J=1.6 Hz). $^{13}$C NMR (CDCl$_3$) δppm: 25.7, 121.7, 123.6, 137.8, 151.4, 155.2, 160.8, 168.9. ES-MS: (M calculated for C$_{10}$H$_8$N$_2$O$_4$: 220.049) found: 221.056 ([MH]$^+$).

N-3-pyridyl-, N'-PEI-thiourea (πPEI) 1

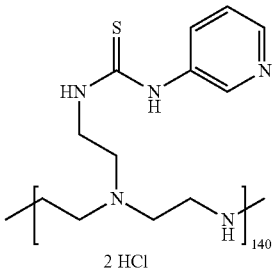

A solution of 3-pyridyl isothiocyanate (460.4 mg; 3.46 mmol) in CH$_2$Cl$_2$ (40 mL) was added dropwise and at room temperature to a solution of PEI (500 mg; 11.62 mmol) in CH$_2$Cl$_2$ (40 mL). After 30 minutes reaction, the solvent was evaporated under reduced pressure. The residue was dissolved in water (40 mL) and the solution was adjusted to pH 4.0 by addition of hydrochloric acid 3M. Dialysis against water (1 L volume; 2 changes over 48 h) and freeze-drying gave 650 mg of the pyridyl PEI-thiourea. The modification degree was estimated at 25% relative to ethylenimine. $^1$HNMR (D$_2$O) δppm: 3.95-2.5 (m, 4H, NHCH$_2$CH$_2$NH), 4.2 (t, 0.5H, CH$_2$NCS), 7.5 (m, 0.25H, CHaro), 7.86 (m, 0.25H, CHaro), 8.45 (m, 0.5H, CHaro). λ$_{max}$(ε calculated for ethylenime unit): 245 nm (2660 M$^{-1}$.cm$^{-1}$). Average Molecular Weight (MW): 122.0 g/mol.

N-3-pyridyl-, N'-PEI-thiourea 15% 2

A solution of 3-pyridyl isothiocyanate (230 mg; 1.73 mmol) in CH$_2$Cl$_2$ (50 mL) was added dropwise and at room temperature to a solution of branched polyethylenimine (500 mg; 11.62 mmol) in CH$_2$Cl$_2$ (40 mL). After 30 minutes reaction, TLC indicated full consumption of the isothiocyanate. The solvent was then evaporated under reduced pressure. The residue was dissolved in water (40 mL) and the solution was adjusted to pH 4.0 by addition of hydrochloric acid 3M. Dialysis against water (1 L volume; 2 changes over 48 h) and freeze drying gave 515 mg of pyridyl PEI-thiourea 15%. $^1$HNMR (D$_2$O) δppm: 4.02-2.65 (m, 4H, NHCH$_2$CH$_2$NH) 4.24 (t, 0.3H, CH$_2$NCS), 7.82 (m, 0.15H, CHaro), 9.1-8.1 (m, 0.3H,CHaro). MW: 100 g/mol.

N-4-aminophenyl, N'-PEI-thiourea 3

A solution of tert-butyl 4-isothiocyanatophenylcarbamate (500 mg; 2.02 mmol) in CH$_2$Cl$_2$ (50 mL) was added dropwise to a solution of PEI (265 mg; 6.16 mmol) in CH$_2$Cl$_2$ (40 mL). The reaction was then stirred for 30 min at room temperature and the solvent was removed by evaporation under reduced pressure. The residue was dissolved in aqueous HCl 3 M (30 mL) and the solution was carefully adjusted to pH 4.0 with aqueous NaOH 6 M. Dialysis against water (2 changes over 24 h) and freeze dried provided N-(4-aminophenyl), N'-PEI-thiourea (650 mg) as a yellow powder. $^1$H NMR (D$_2$O) δppm: 4.0-2.67 (m, 3.3H, NHCH$_2$CH$_2$NH), 4.21 (m, 0.7H, CH$_2$NCS), 7.35 (bm, 1.4H, CHaro). Average MW: 140 g/mol.

4-hydroxybenzamido-polyethylenimine 4

A solution of freshly prepared 4-hydroxybenzoic acid (635 mg; 4.6 mmol) and BOP (1.7 g; 5.06 mmol) in DMF (20 mL) was added dropwise and at room temperature to a solution of PEI (1 g, 23.2 mmol) in DMF (50 mL). After 2 hours under stirring, the DMF was removed by evaporation under reduced pressure. The crude product was taken in water, dissolved by addition of aqueous sodium hydroxide solution 1M (pH 11) and subjected to dialysis against water (1 L, 2 changes over 24 h). Lyophilization provided 4-hydroxybenzamide-PEI (0.7 g) at a modification degree of 28%. $^1$H NMR (D$_2$O) δppm: 2.6 (bm, 2.9H, —NHCH$_2$CH$_2$NH—), 3.22 (m, 0.55H, Phe-CONHCH$_2$CH$_2$NH—), 3.35 (m, 0.55H, Phe-CONHCH$_2$CH$_2$NH) 6.57 (d, J=7.3 Hz, 0.55H, CHaro), 6.97 (m, 0.55H, CHaro).

Vanillamido-polyethylenimine 5

A solution of succinimidyl ester of vanillic acid (2.8 g, 10.5 mmol) in DMF (20 mL) was added at room temperature to a solution of polyethylenimine (0.9 g, 20.9 mmol in ethylenimine) in methanol (5 mL). After 2 days stirring, the residue was treated with NaOH 1M (5 mL) for 1 h at room temperature. The pH of the solution was then adjusted to pH 7.0 by addition of aqueous 0.5 M HCl and the solution was subjected to dialysis against water (1 L, 5 changes over a 48 h period). Lyophilization afforded the product as yellow powder (1.4 g, 67% yield). $^1$H NMR (D$_2$O) δppm: 2.0-3.9 (16H), 6.6 (s br, 1H), 6.9-7.4 (m, 2H). $^{13}$C NMR (D$_2$O) δppm: 36.6, 49.9, 56.0, 115.0, 121.0, 146.9, 150.3. λ$_{max}$(ε calculated for ethylenime unit): 290 nm (2000 M$^{-1}$.cm$^{-1}$), 260 nm (4000 M$^{-1}$.cm$^{-1}$). Average MW: 127 g/mol.

2-hydroxybenzamido-polyethylenimine 6

A solution of succinimidyl ester of salicylic acid (1.47 g, 6.2 mmol) in DMF (15 mL) was added at room temperature to a solution of polyethylenimine (0.9 g, 20.9 mmol in ethylenimine) in CH$_2$Cl$_2$ (3 mL). Two hours later, the reaction mixture was completed with methanol (20 mL) and stirred for 24 h. The solvents were removed under reduced pressure and the residue was treated with NaOH 1M (20 mL). The solution was subjected to dialysis against water (1 L, 2 changes over a 24 h period), aqueous HCl (1 L, 6 changes over a 48 h period) and water (1 L, once for 6 h). Lyophilization afforded the product as a powder (1.8 g, 86% yield). $^1$H NMR (D$_2$O) δppm: 2.0-3.9 (13.2H), 6.7-7.6 (m, 4H). $\lambda_{max}$(ε calculated for ethylenime unit): 300 nm (790 M$^{-1}$.cm$^{-1}$). Average molecular weight: 117 g/mol.

Nicotinamido-polyethylenimine 7

A solution of succinimidyl ester of nicotinic acid (3.52 g, 16 mmol) in DMF (15 mL) was added at room temperature to a solution of polyethylenimine (1.4 g, 32 mmol in ethylenimine) in CH$_2$Cl$_2$ (10 mL). Two hours later, the reaction mixture was completed with methanol (20 mL) and stirred for 24 h. The solvents were removed under reduced pressure and the residue was treated with NaOH 1M (20 mL). The solution was subjected to dialysis against water (1 L, 2 changes over a 24 h period), aqueous HCl (1 L, 6 changes over a 48 h period) and water (1 L, once for 6 h). Lyophilization afforded the product as a powder (2.2 g, 75% yield). $^1$H NMR (D$_2$O) δppm: 2.6-3.9 (10.1H), 7.1-9.0 (m, 4H). $\lambda_{max}$(ε calculated for ethylenime unit): 260 nm (1800 M$^{-1}$.cm$^{-1}$). Average MW: 112 g/mol.

Figure 16:
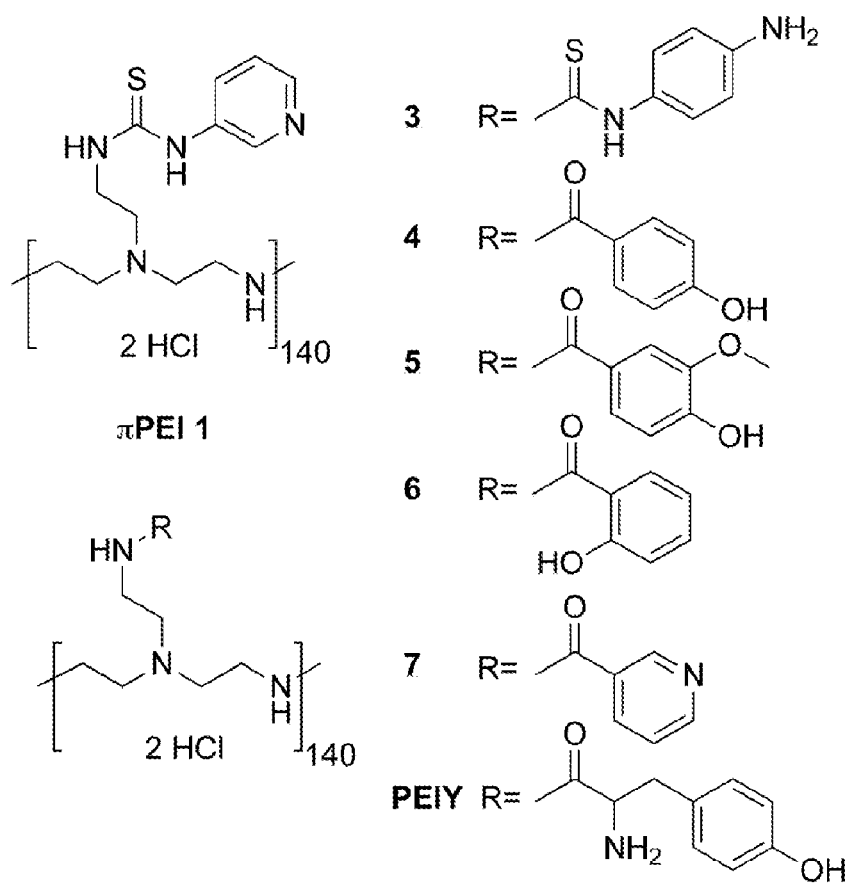
FIG. 16: Chemical structure of the siRNA delivery polyethylenimines: N-3-pyridyl-, N'-PEI-thiourea (πPEI) 1; N-4-aminophenyl, N'-PEI-thiourea 3; 4-hydroxybenzamido-polyethylenimine 4; Vanillamido-polyethylenimine 5; 2-hydroxybenzamido-polyethylenimine 6; Nicotinamido-polyethylenimine 7 and PEIY (Creusat and Zuber, 2008). Polymers were modified at about 30% extend relative to ethylenimine residues, except for nPEI 2, which was modified at 15%.

Structures of compounds 1, 3, 4, 5, 6 and 7 are presented on FIG. 16.

Materials for the siRNA Delivery Experiments

PAGE-purified oligonucleotides were terminated at 3'-ends with two 2'deoxythymidines. They were purchased from Eurogentec (Seraing, Belgique), supplied at 100 μM concentration and stored at −20° C. The egfpluc fusion gene was silenced with a RNA duplex of the sense sequence (si-luc): 5'-CUU ACG CUG AGU ACU UCG A (SEQ ID NO:1). Untargeted RNA duplex (sic) was of sequence 5'-CGU ACG CGG AAU ACU UCG A (SEQ ID NO:2). Polymers were dissolved in water. The solutions were adjusted to pH 6.0 with NaOH 1M and the final polymer stock concentration was of 0.2 M in ethylenimine except for 6 (50 mM). Solutions were stored at 4° C. Cells were maintained at 37° C. in a 5% CO$_2$ humidified atmosphere and were grown in DMEM medium with 10% Fetal bovine serum (FBS) (Perbio, Brebières, France), 100 units/mL penicillin, 100 μg/mL streptomycin and 2 mM L-glutamine (Eurobio, Courtaboeuf, France). U87 cells (human glioblastoma ATCC) were transformed to stably express the Photinus pyralis luciferase-enhanced green fluorescence protein fusion gene originating from the pEGFPluc plasmid (Clontech, Mountain View, Calif.). The plasmid codes as well for a resistance gene to G418 and selection was by addition of 0.8 mg/mL G418 to the cell culture medium. A549Luc cells (human lung carcinoma; CCL-185; ATCC) were transformed to stably express the Photinus pyralis luciferase gene originating from the pGL3 plasmid (Clontech, Mountain View, Calif.) and a resistance gene against G418. A549Luc cells were grown in RPMI 1640 medium. Hela cells were grown in DMEM medium. U87egfpluc cells were seeded into 96-well plates the day before experiments at a density of 8,000 cells per well in 100 μL cell culture medium.

Determination of Polyplexes Stability

Polyplexes were prepared by mixing the control siRNA (735 ng, 50 pmol) and each polymer (100 nmol in ethylenimine) either in RPMI (15 μL, final pH of 7.8) or in water (15 μL, final pH of 6.0). After 20 minutes incubation, the polyplexes were treated with increasing charge excess of heparin, for 30 min, loaded onto a 2% agarose gel containing 1 mM EDTA and 40 mM Tris acetate buffer pH 8.0, and subjected to electrophoresis for 30 min at 90 V. After staining with ethidium bromide solution (0.5 μg/mL, 15 min), released siRNA were visualized with a UV transilluminator and quantified using NIH ImageJ analysis software.

Determination of the Polymer Toxicity (MTT Assay)

The MTT assay was performed in triplicate in 96 wells-plates. The polymers (11 μL), at different concentrations, were added to the cells to obtain the final concentration as indicated in the graph. After incubation of the cells for 48 h, the cell culture medium was removed from each well and replaced with a 0.5 mg/mL MTT solution in DMEM without serum (220 μL). After 2 h incubation at 37° C., excess reagent was removed by aspiration. The formazan crystals were dissolved in DMSO (100 μL) and were quantified spectrophotometrically in a microplate reader at a wavelength of 570 nm. The cell viability was plotted relative to untreated cells that were grown the same day in the same plate.

Hemolysis Experiments

Before experiments, sheep red blood cells (RBC) (Eurobio, Courtaboeuf, France) were recovered by centrifugation at 400 RCF for 10 min and washed three times with NaCl aqueous solution (150 mM). RBC were then resuspended in phosphate buffer saline (PBS) and plated in 96-well plates to obtain 15×10$^6$ cells in 50 μL. 50 μL of polymer solutions at different concentrations, also prepared in the same phosphate buffer, were added to the erythrocytes and incubated for 1 h at 37° C. The release of hemoglobin was determined after centrifugation at 700 RCF for 10 min by spectrophotometric analysis of the supernatant at 550 nm. Complete hemolysis (100% control value) was achieved using TritonX100 to a final concentration of 0.1% w/v. The negative control was obtained by suspension of RBC in phosphate buffer alone. The experiments were performed in triplicate.

SiRNA Delivery Experiments In Vitro

Typically, an aqueous solution of the polymer (10 mM in ethylenimine) (0.96 μL) was added to a 100 nM solution of siRNA in RPMI medium without serum (40 μL). After agitation, the complexes (11 μL containing 16.17 ng siRNA) were added into a well by dilution with the cell. Alternatively, polyplexes prepared for in vivo injection (2 μL) were diluted in 10% FBS cell culture medium (100 μL). After agitation, the complexes (10 μL) were then immediately added to the cells medium containing serum (0.1 mL). Cells were then let to grow in the incubator without further handling. Luciferase gene expression was usually determined 48 h after delivery with a commercial kit using manufacturer's protocol (Promega, Charbonnières, France). The luminescence was measured from 1 μL of lysate during is with a luminometer (Centro LB960 XS; Berthold, Thoiry, France). The errors bars represent standard deviation derived from triplicate experiments and efficiency was calculated relative to untreated cells.

Cytometry Analysis

Analysis of EGFP production was measured 72 h after addition of the complexes into the 96 wells-plates. Cell media were removed. The adherent cells were then washed once with PBS (100 μL), detached with a 0.2% trypsin solution (20 μL) for 10 minutes and taken in DMEM containing serum (100 μL) for immediate analysis on a Millipore-Guava Easy-Cyte capillary cytometer equipped with a blue laser (488 nm excitation wavelength).

Size Measurement

The apparent sizes were determined via dynamic light scattering measurements using a NanoZS apparatus (Malvern instruments, Paris, France) at 25° C. using a refractive index of particles of 1.49. Data were analyzed using the multimodal number distribution software included with the instrument. πPEI/siRNA complexes (50 μL) prepared for in vivo injection were diluted in 0.9 mL of 4.5% glucose right before measurement. πPEI/siRNA polyplexes prepared in RPMI (100 μL) were diluted in RPMI (0.9 mL).

SiRNA Delivery Experiments In Vivo

Polyplexes were formed at room temperature by mixing a 100 μM siRNA solution (80 μL) with a 9% (w/v) glucose solution (100 μL). This mixture was then rapidly added to 20 μL of a 150 mM (18.3 mg/mL) πPEI solution, pH 6.0. Particles were injected 20 min later. Male nude mice (6-8 weeks of age, weights in the 25-30 g) were subcutaneously inoculated in both flanks with 5×10$^6$ U87egfpluc cells in 100 μL PBS. Mouse behavior and weight were monitored every 2 to 4 days and tumor growth was evaluated with a digital caliper. Tumor volume was calculated using the formula [(length× width$^2$)×0.52]. 25 days after inoculation, mice were anaesthetized using isoflurane and complexes (40 μL) were injected into the tumor mass of average volume of 260 mm$^3$ using a 0.3 mL syringe equipped with a 30G needle (BD MicroFine, Becton Dickinson, Franklin Lakes, N.J., USA). Mice were anaesthetized again 4 days later. The volume of tumors was measured and the animals were sacrificed by cervical dislocation. The tumors were dissected, washed in PBS and cut in two pieces. One piece was fixed in PFA for histological analysis. The other piece was wiped up with an adsorbing paper and freeze-dried in liquid nitrogen. For luciferase activity measurement, the freeze-dried tumor was weighted, diluted in cold PBS at 80 mg of tumor/mL, grinded with a T25 ultra-turrax at 0-4° C. and the solutions clarified by centrifugation (10,000 RCF, 10 min). Luciferase activity of the supernatant was measured and expressed as relative light units (RLU) integrated over 10s and normalized per μg of tumor protein by using the BCA assay (Pierce, Brebières, France). Statistical analysis (Student t-Test) and calculation of the t probability (p) were performed using KaleidaGraph Software 4.1 on paired data.

Results and Discussion

Design and Synthesis of the Polymers

Most synthetic delivery systems use initial electrostatic anchorage to sulfated (polyanionic) proteoglycans present on the external cell surfaces to accumulate in large amounts into endosomes. Use of this route relies on cationic complexes stable enough to sustain electrostatic competition with the external polyanionic cell surface receptors but capable of dissociation inside the cell for payload delivery. After cell anchorage to anionic proteoglycans, polyplexes can be directed into endosomal compartments and senses a pH-decrease from pH 7.4 to 4.5. It has been previously demonstrated that PEI polyplexes interfere with the normal acidification process. The buffering ability of PEI blocks the cell-induced endosomal acidification at measured pHs of 5.9 or 6.1, leading eventually to rupture of the endosome membrane and an access to the cytosol. Chemical modification of the water soluble polyethylenimine (PEI) with tyrosine improves considerably its oligonucleotide delivery abilities at a cellular level (Creusat and Zuber, 2008). Mechanistic investigations suggested that the high efficacy of this PEI-tyrosine conjugate (PEIY) is related to siRNA polyplexes stable in extracellular media but unstable in acidic endosomes. This allows high internalization of siRNA polyplexes into endosomes while favoring nucleic acids release upon PEI-mediated endosomolysis. At a starting point, the inventors explored variation in the chemical structure of the PEI-grafted hydrophobic domains and in the type of conjugation linkage for possible improvement of delivery activity and/or toxicological profile. To simplify preparation and comparison, the various hydrophobic elements were grafted to the commercial branched 25 KDa PEI at a content of 30% relative to ethylenimine unit (EI). In principle, this value corresponds to a full modification of the PEI primary amines. The first polymer, named πPEI 1 was prepared by reaction with 3-pyridyl-isothiocyante (0.3 equivalent relative to PEI ethylenimine unit) in a DMF/dichloromethane.

To evaluate the effect of the degree of modification, the same reaction was performed with a two fold decrease in the isothiocyanate input relative to PEI to provide the polymer πPEI 2 with a modification degree of 15%. The third polymer 3 was prepared from N-tert-butyloxycarbonyl-4-aminophenylisothiocyanate and obtained after removal of the protecting group with trifluoroacetic acid. The polymer 4 was prepared from 4-hydroxybenzoic acid using Benzotriazole-1-yl-oxy-tris-(dimethylamino)-phosphonium hexafluorophosphate (BOP) as the condensing reagent. Finally, the polymers 5, 6 and 7 were prepared by reacting PEI with succinimidyl esters of vanillic acid, salicylic acid and nicotinic acid, respectively, also in DMF/dichloromethane.

After completion of the reactions, each polymer was purified by dialysis and isolated as hydrochloride salts. Yields were typically in the 50-60% range and $^1$H NMR integration of characteristic peaks confirmed the modification degree to be close to the expected value of 15% for 2 and 30% for all the others. Each polymer was then analyzed by agarose gel electrophoresis for their abilities to form electrostatic complexes with oligonucleotides. Regardless of the modification, the onset of full complexation intervenes at EI to oligonucleotide phosphate (P) ratio of 3.0 (data not shown).

siRNA Delivery Ability

Figure 17:
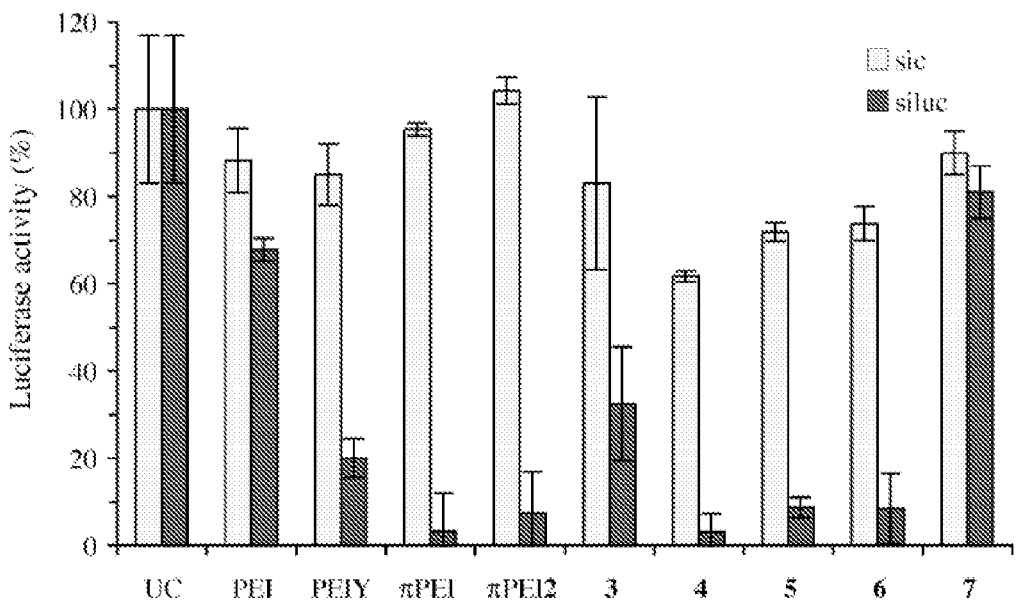
FIG. 17: Efficiency of the various polymers to deliver siRNA into U87 cells that were stably transformed to express an egfpluc fusion protein (U87egfpluc). Each polymer was mixed with either luc-targeting siRNA (siluc) or untargeting siRNA (sic) and added to cells. Luciferase activity was measured 48 h later. Final concentrations are 10 nM in siRNA and 24 µM in the indicated polymers. (24 µM correspond to 3 µg/mL polymer).

SiRNA duplexes can effectively and selectively silence the expression of a gene only if the duplexes can be transferred into the cell. The delivery abilities of the polymer were hence directly deducted by measuring the siRNA-mediated silencing of a luciferase-enhanced green fluorescent chimera gene using either targeting (siluc) or control (sic) siRNAs. To avoid flaws from transient transfection experiment, the human gliobastoma U87 cell line was transformed to stably express a luciferase-green fluorescent protein chimera originating from the pEGFPLuc plasmid. The resulting U87egfpluc has the advantage to express a fusion protein that can be silenced with a unique targeted siRNA and quantify either by monitoring the green fluorescent protein or by measuring the enzymatic activity of the firefly luciferase domains. SiRNAs polyplexes were prepared by mixing the polymer to a final concentration of 240 μM in ethylenimine unit with 100 nM siRNA in RPMI cell culture medium. The resulting cationic polyplexes with a ethylenimine to siRNA phosphate ratio of 60 were then simply added to cells by dilution with the serum-containing cell culture medium to reach a final siRNA concentration of 10 nM. Forty-eight hours later, the luciferase activity of the cell lysate was measured and expressed relative to untreated cells (UC) (FIG. 17). As previously observed (Grayson et al., 2006), unmodified PEI shows to be a poor in vitro siRNA carrier. PEIY, πPEI 1 (also named πPEI) and hydroxybenzamido-PEI derivatives 4, 5 and 6 enabled a significant and selective siluc-mediated luciferase silencing. Decreasing the pyridylthiourea content on PEI (πPEI 2) diminishes slightly the siRNA-mediated luciferase gene silencing while a more dramatic diminution was obtained with the polymer 3.

Evaluation of siRNA/PEIY Polyplexes Stability

The electrostatic stability of the siRNA polyplexes upon interaction with sulfated proteoglycans present on the external cell surface membrane and in PEI-loaded endosomes was examined in the RMPI cell culture medium pH 7.8 or at pH 6.0, respectively, by competition with heparin (Dufresne et al., 2008). The siRNA polyplexes from πPEI, 6 or 7 were prepared at an EI/P ratio of 50 and the cationic particles were incubated with increasing amounts of the sulfated polysaccharide heparin and release of siRNA was quantified from agarose gel electrophoresis assays (FIG. 18). Results showed siRNA polyplexes made from 7 to dissociate almost quantitatively upon challenge with heparin, even at pH 7.8, suggesting that its weak siRNA delivery efficacy is due to a too early extracellular siRNA release. In contrast, the effective siRNA delivery polymers πPEI and 6 improve the electrostatic cohesion of the siRNA/pPEI complexes at pH 7.8 while allowing siRNA release at pH 6.0. This experiment confirmed that assembly but also disassembly can be rendered pH sensitive by modifying the hydrophobic/hydrophobic balance of PEI and taking advantage of its solubilization upon endosomal buffering.

Cytotoxicity and Hemolytic Activity

Cytotoxicity can be a limiting factor for the development of any drug carrier. Polycations and especially the ones used for nucleic acid delivery are known to damage cellular membranes (Fischer et al. 2003; Hong et al., 2006) and to induce cell death (Fischer et al., 2003). The potential damaging effect of PEI, 6, πPEI and PEIY on cellular membranes was estimated from hemolysis assays using sheep red blood cells (FIG. 19A). The results show PEI, but also the hydroxyphenyl-possessing 6 and PEIY polymers to possess a hemolytic activity at concentrations above 1 mg/mL. In contrast, the πPEI did not induce any release of heme from the red blood cells up to a concentration level of 5,000 μg/mL. This result suggests that πPEI, which as the same delivery activity as PEIY and 6, is the most suitable carrier for in vivo administration. Next, the cytotoxicity of πPEI was compared to that of PEI by exposing the U87-egflpuc to increased concentration of each polymer. The cell viability was then extrapolated 48 h later by measuring the cellular mitochondrial activity using the MTT reagent (FIG. 19B). Both polymers affect the cell viability with a sigmoidal type dose-response profile, as previously observed on other cell lines. The πPEI polymer appears toxic to U87 cells ($IC_{50}$=90 μg/mL) but less than PEI ($IC_{50}$=40 μg/mL) and at concentration much above than the utilized πPEI final concentration of 3 μg/mL for siRNA delivery.

Preparation of Complexes for In Vivo Administration

The previous experiments show πPEI to be an excellent in vitro siRNA delivery vehicle with a favorable toxicological profile. Cumulative experience with PEI for in vivo delivery of nucleic acid suggests to prepare nucleic acid polyplexes with N/P ratio of 10 and at a much higher PEI concentration of 1-2 mg/mL versus 0.03 mg/mL for in vitro (Goula et al., 1998; Hobel et al., 2010). However, increased concentrations impact the kinetic and assembly processes. Polyplexes, and especially ones made from self-assembling polymers, can grow to sizes too large for cell engulfing. For instance, self-assembly of πPEI in RPMI for in vitro experiments (29.3 μg/mL or 0.24 mM in EI) yielded to particles with an average diameter of 240 nm after 30 min incubation (Table 3 below). Inclusion of siRNA within polyplexes led to slight plumpness but did not modify drastically the overall slow aggregation kinetic. Self-assembly of the polymer in the RPMI medium but at a higher concentration of 1.83 mg/mL occurs much faster and useless particles with diameter of 1,200 nm (PDI=0.197) were already measured after 30 minutes incubation. To minimize particle growth, one solution is to assemble the cationic polyplexes in solutions containing no electrolytes because the strong electrostatic repulsion between cationic species limits collision and enables preparation of stable colloids (Goula et al., 1998). The πPEI was therefore buffered to pH 6.0 to ensure full water solubility and the siRNA polyplexes were assembled in isotonic glucose solution at a EI/P ratio of 9.4. Dynamic light scattering (DLS) data (Table 3 below) showed that this conditions yielded particles with diameter of about 100 nm at a high polymer concentration of 1.83 mg/mL.

TABLE 3

Effect of the medium and concentrations of the partners on the formation of the polyplexes. Diameters were determined from light scattering data

| Duration of incubation | Polyplexes for in vitro use, prepared in RPMI, pH 7.8[1] | | Polyplexes for in vivo, prepared in 4.5% glucose[2] | |
|---|---|---|---|---|
| | πPEI | πPEI/siluc | πPEI | πPEI/siluc |
| 0.5h | 240 nm PDI: 0.256 | 310 nm PDI: 0.38 | (—)[3] | 90 nm PDI: 0.183 |
| 2h | 360 nm PDI: 0.370 | 360 nm PDI: 0.420 | (—)[3] | 96 nm PDI: 0.260 |

[1]Conditions: 0.24 mVI πPEI without or with 0.1 μM siRNA in RPMI, pH 7.8.
[2]Conditions: 15 mM πPEI, pH 6.0, without or with 40 μM siRNA.
[3]Scattering signal too weak.

Figure 20A:
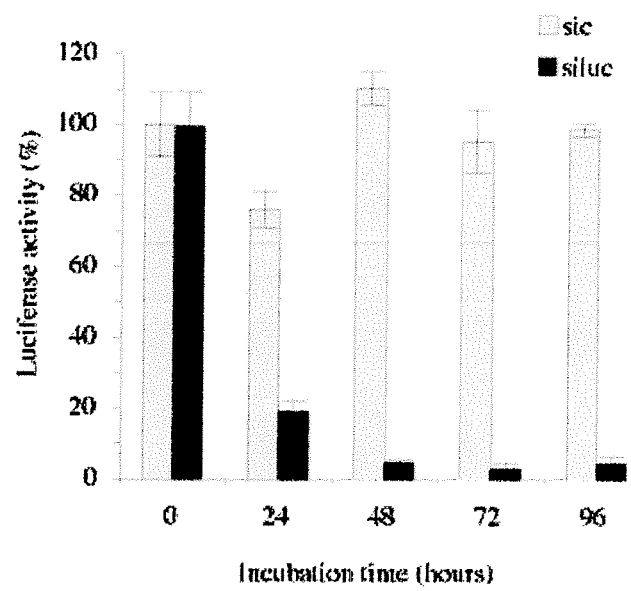
FIG. 20A. Duration of siRNA-mediated luciferase silencing using πPEI (A) and effect of the polyplex preparation procedure on the silencing efficiency (B and C). (πPEI/siluc) were prepared in RPMI medium with 30 µg/mL πPEI and diluted to final concentration of 3.0 µg/mL πPEI and 10 nM siRNA. πPEI/siRNA i.v. were prepared in 4.5% glucose solution with 1830 µg/mL πPEI (same condition as the injected polyplexes) and diluted to final concentrations of 3.3 µg/mL πPEI and 72.7 nM siRNA.
Figure 20B:
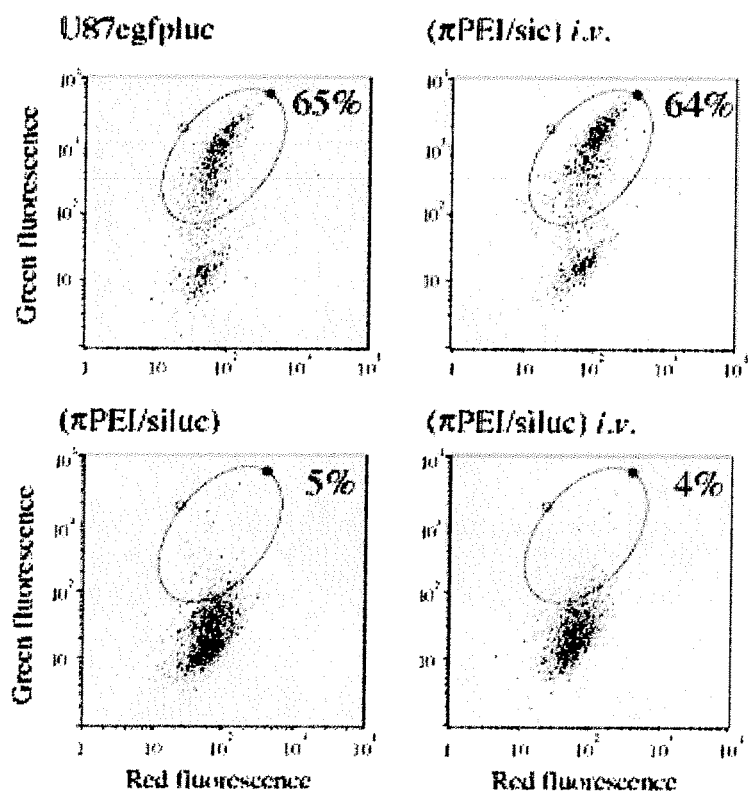
FIG. 20B. Green fluorescent protein-expressing cells were monitored by capillary cytometry analyses 72 h after addition of the indicated polyplexes.
Figure 20C:
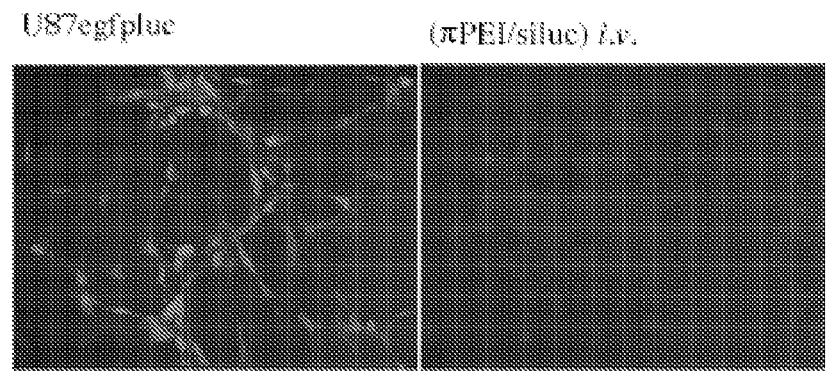
FIG. 20C. Fluorescence microscopy images of living U87efpluc cells incubated for 48 h without and with πPEI/siRNA i.v.

Having determined the conditions to prepare siRNA polyplexes with suitable sizes form possible worming their way into dense tri-dimensional tissues, the duration of siRNA-mediated luciferase gene silencing after carriage with πPEI was evaluated (FIG. 20A). πPEI showed to assist a selective siRNA-mediated luciferase gene silencing whereas delivery of an untargeted siRNA (sic) did not diminish the cellular luciferase activity over the experiment time course. Maximum protein activity inhibition was reached 48 h after administration (superior to 90%) and lasted at least 4 days. Next, the efficiency of the siluc/πPEI polyplexes prepared at a polymer concentration of 1.8 mg/mL in glucose (noted as i.v.) was compared to the ones prepared at 0.029 mg/mL in RPMI. To obtain complementary information, the inventors measured this time the expression of the green fluorescent protein of the U87egflpluc after dilution with the serum containing cell culture medium to similar final πPEI concentrations. Capillary flow cytometry analysis (FIG. 20B) and fluorescent optical microscopy (FIG. 20C) showed a remarkable silencing effect spread over the entire cell population regardless of the mode of preparation.

In Vivo Experiment

Figure 21A:
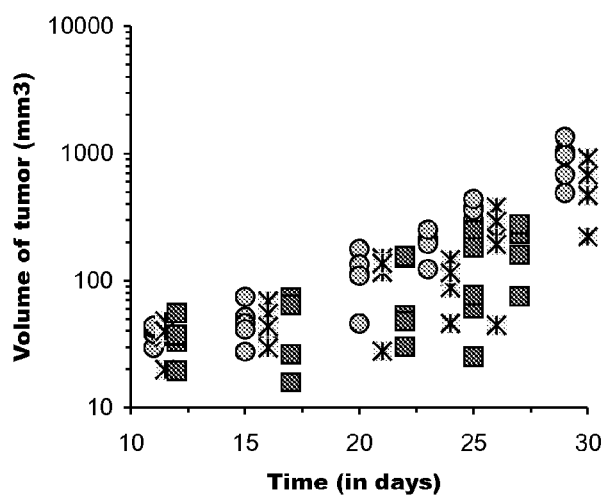
FIG. 21A. Growth of U87egfpluc tumors xenografted in athymic mice. Cells were inoculated at day 0. Polyplexes (72 µg πPEI, 23.5 µg siRNA in 40 µL 4.5% glc) were injected into the solid tumor 25 days after inoculation.
Figure 21B:
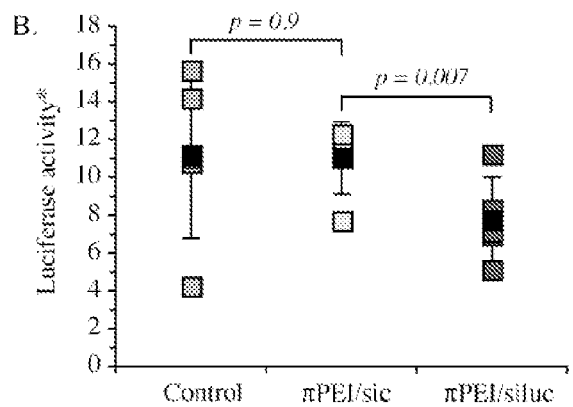
FIG. 21B. Luciferase activity of the U87egfpluc tumors 4 days after polyplex injection (in MegaRLU/10s/µg tumoral protein).
Figure 22:
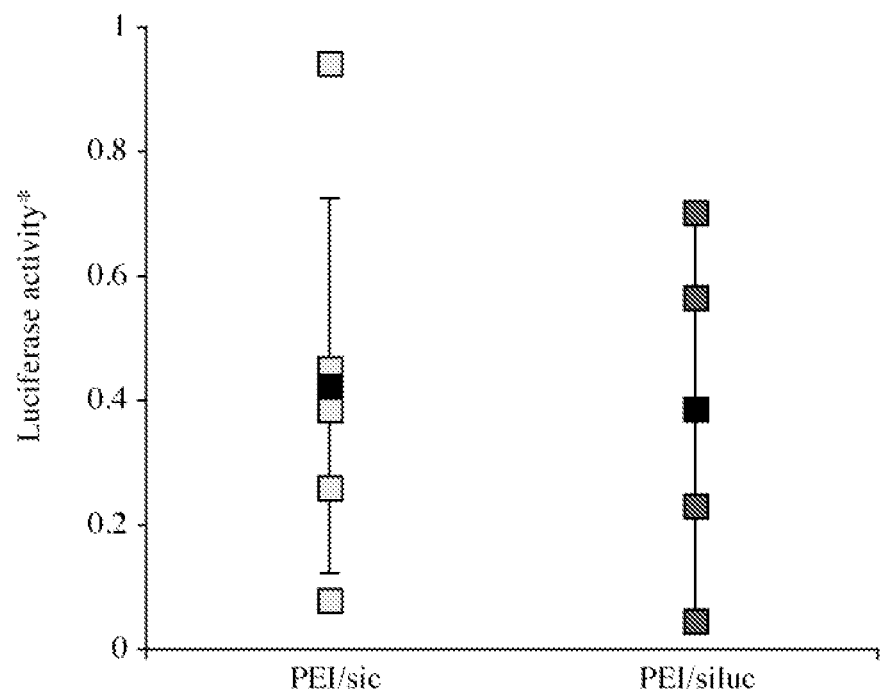
FIG. 22: Luciferase activity (in MegaRLU/10s/µg tumoral protein) of the U87egfpluc tumors 4 days after the $2^{nd}$ intra-tumoral injection. One injection consists in the indicated PEI/siRNA polyplexes (72 µg PEI, 23.5 µg siRNA in 40 µL 4.5% glc). The solutions were injected into the solid tumor. Results showed that PEI does not assist a selective siRNA-mediated luciferase silencing on the U87egfpluc tumor model upon intratumoral injection.

The final experiment was to demonstrate the potential of πPEI to carry siRNA to mice-xenografted U89egfpluc cells. The model was done by subcutaneously injection of U87egfpluc human glioblastoma cells into flanks of athymic mice and leaded to well-developed solid tumors with exponential growth mode (FIG. 21A). For therapeutic purpose, systemic injection is the ideal administration mode. However, cationic polyplexes are known to promote erythrocyte aggregation, to dissociate in the blood and to accumulate preferentially in lung or liver, leading to possible systemic toxicity and overall limited accumulation of particles into the xenografted tumor. As recommended, the inventors chose to bypass these problems this various problems and chose to administer the siRNA polyplexes directly into the tumors. A single dose of siRNA polyplexes (23.5 μg of either targeted siluc or untargeted sic siRNAs complexed with 72 μg πPEI, pH 6.0 in 40 μL 4.5% glucose) was slowly injected into tumors of average volume of 260 mm$^3$. 4 days later, the tumor growth and the luciferase activity of the U87egfpluc tumors were measured and reported in FIG. 21. Injection of the complexes did not appear to restrain the exponential growth of the tumors (FIG. 21A) or to modify the behavior or weights of mice. Yet, a significant and selective luciferase gene silencing of 30% was observed with the siluc/πPEI polyplexes by comparison to controls (FIG. 21B). Next, and although it is difficult to extrapolate from negative values, on the present particular model (U87 cell, intratumoral injection), PEI did not significantly assist a selective siRNA-mediated luciferase gene (FIG. 22).

Figure 23:
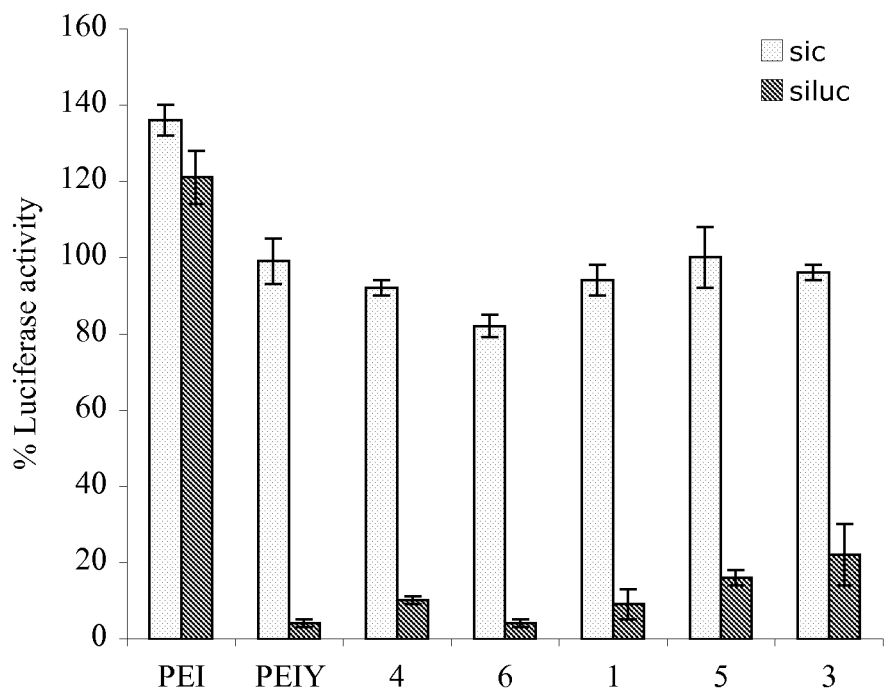
FIG. 23: Evaluation of the various polymer to deliver siRNA into A549 cells. Luciferase-Targeting (siluc) on untargeted (sic) siRNAs (6 pmol, 88 ng) were formulated with the indicated polymer (12 nmol) in RPMI and added to A5461uc cells. Cells were seeded the day before at 25,000 cells per well in 24 well-plates and were stably transformed to express an endogenous luciferase gene. Luciferase gene expression was measured 48 h and efficiency of the overall gene silencing process was relative to untreated cells.
Figure 24:
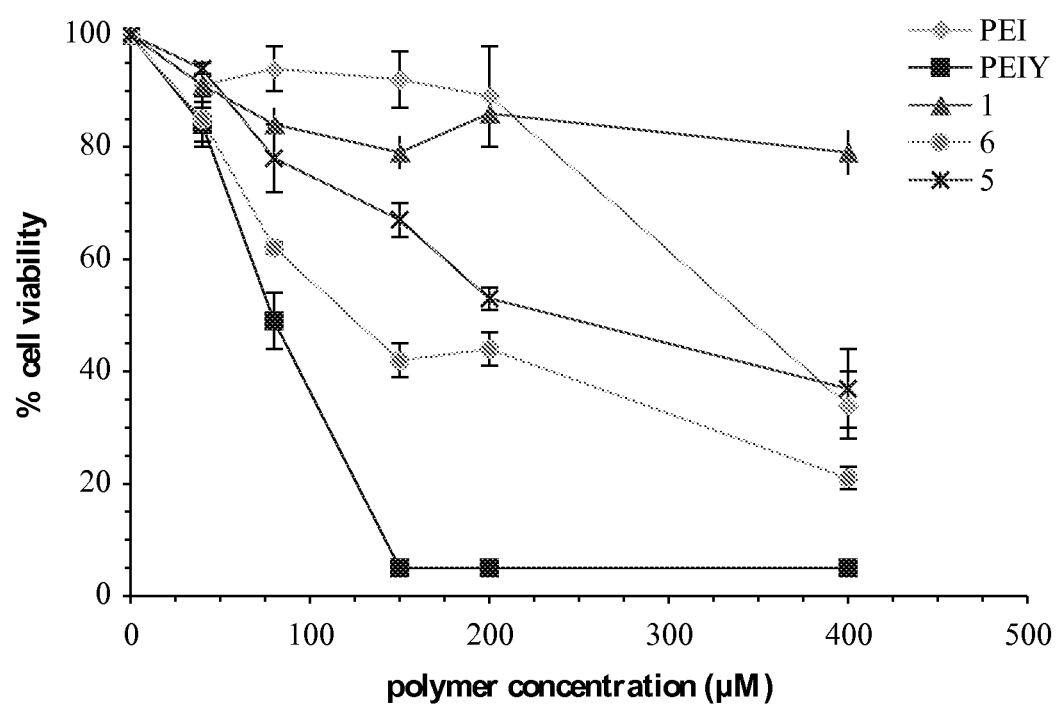
FIG. 24: Estimation of Hela cell viability in the presence of increasing concentrations of various PEIs, as indicated. Cell viability was estimated by measuring the redox activity of living cells using the 3-(4,5-Dimethylthiazol-2-yl)-2,5-diphenyltetrazolium bromide (MTT) reduction assay.

Next, the inventors evaluated the efficacy of the polymer to deliver siRNA in human alveolar basal epithelial cells (A549 cells). FIG. 23 shows the polymers 1, 3, 5, 6 (see FIG. 16 for chemical structure) to permit an effective transport of oligonucleotides into the cytosol of these cells as seen by their properties to mediate a selective siRNA-mediated gene silencing. Finally, the FIG. 24 shows that the polymer 1, but also the polymers 5 and 6 to be less toxic to Hela cells than tyrosine-modified PEI, confirming that they present a favorable toxicological profile This invention has been described with reference to various specific and exemplary embodiments and techniques. However, it should be understood that many variations and modifications will be obvious to those skilled in the art from the foregoing detailed description of the invention and be made while remaining within the spirit and scope of the invention.

REFERENCES

Akinc, A., Thomas, M., Klibanov, A. M., and Langer, R. (2005) Exploring polyethylenimine-mediated DNA transfection and the proton sponge hypothesis. *J Gene Med* 7, 657-63.

Berge, et al. J. Pharmaceutical Sciences, 1977, 66: 1-19.

Bolcato-Bellemin, A. L., Bonnet, M. E., Creusat, G., Erbacher, P., and Behr, J. P. (2007) Sticky overhangs enhance siRNA-mediated gene silencing. *Proc Natl Acad Sci USA* 104, 16050-5.

Creusat, G., and Zuber, G. (2008) Self-assembling polyethylenimine derivatives mediate efficient siRNA delivery in mammalian cells. *Chembiochem* 9, 2787-9.

Dufresne, M. H., Elsabahy, M., Leroux, J. C. (2008), Characterization of polyion complex micelles designed to address the challenges of oligonucleotide delivery. *Pharm Res* 25, (9), 2083-93

Felgner, P. L. (1999) Prospects for synthetic self-assembling systems in gene delivery. *J Gene Med* 1, 290-2.

Fraley, A. W., Pons, B., Dalkara, D., Nullans, G., Behr, J. P., and Zuber, G. (2006) Cationic Oligonucleotide-Peptide Conjugates with Aggregating Properties Enter Efficiently into Cells while Maintaining Hybridization Properties and Enzymatic Recognition. *J Am Chem Soc* 128, 10763-71.

Fischer, D., Li, Y., Ahlemeyer, B., Krieglstein, J., Kissel, T. (2003) In vitro cytotoxicity testing of polycations: influence of polymer structure on cell viability and hemolysis. *Biomaterials* 24, (7), 1121-31

Goula, D.; Remy, J. S.; Erbacher, P.; Wasowicz, M.; Levi, G.; Abdallah, B.; Demeneix, B. A. (2006) Size, diffusibility and transfection performance of linear PEI/DNA complexes in the mouse central nervous system. *Gene Therapy* 712-717.

Grayson, A. C., Doody, A. M., and Putnam, D. (2006) Biophysical and structural characterization of polyethylenimine-mediated siRNA delivery in vitro. *Pharm Res* 23, 1868-76.

Hobel, S., Koburger, I., John, M., Czubayko, F., Hadwiger, P., Vornlocher, H. P., Aigner, A. (2010), Polyethylenimine/small interfering RNA-mediated knockdown of vascular endothelial growth factor in vivo exerts anti-tumor effects synergistically with Bevacizumab. *J Gene Med* 12, (3), 287-300.

Hong, S., Leroueil, P. R., Janus, E. K., Peters, J. L., Kober, M. M., Islam, M. T., Orr, B. G., Baker, J. R., Jr., Banaszak Holl, M. M. (2006), Interaction of polycationic polymers with supported lipid bilayers and cells: nanoscale hole formation and enhanced membrane permeability. *Bioconjug Chem* 17, (3), 728-34.

Kang, S. H., Cho, M. J., and Kole, R. (1998) Up-regulation of luciferase gene expression with antisense oligonucleotides: implications and applications in functional assay development. *Biochemistry* 37, 6235-9.

Kurreck, J. (2003) Antisense technologies. Improvement through novel chemical modifications. *Eur J Biochem* 270, 1628-44.

Kurreck, J. (2003) Nucleic acids chemistry and biology. *Angew Chem Int Ed Engl* 42, 5384-5.

Neu, M., Fischer, D., and Kissel, T. (2005) Recent advances in rational gene transfer vector design based on poly(ethylene imine) and its derivatives. *J Gene Med* 7, 992-1009.

Sonawane, N. D., Szoka, F. C., Jr., and Verkman, A. S. (2003) Chloride accumulation and swelling in endosomes enhances DNA transfer by polyamine-DNA polyplexes. *J Biol Chem* 278, 44826-31.

Valeur, E., Bradley, M. (2009) Amide bond formation: beyond the myth of coupling reagents. *Chem. Soc. Rev.* 38, 606-631.

Verma, S., and Eckstein, F. (1998) Modified oligonucleotides: synthesis and strategy for users. *Annu Rev Biochem* 67, 99-134.

Williams, J. H., Sirsi, S. R., Latta, D. R., and Lutz, G. J. (2006) Induction of dystrophin expression by exon skipping in mdx mice following intramuscular injection of antisense oligonucleotides complexed with PEG-PEI copolymers. *Mol Ther* 14, 88-96.

Zimmermann, T. S., et al. (2006) RNAi-mediated gene silencing in non-human primates. *Nature* 441, 111-4.

The invention claimed is:

1. A polyethylenimine having multiple amine functions modified or substituted by a radical X, wherein X is C(=Z)—R₁ wherein

Z is S or O; and

R1 is selected from the group consisting of:

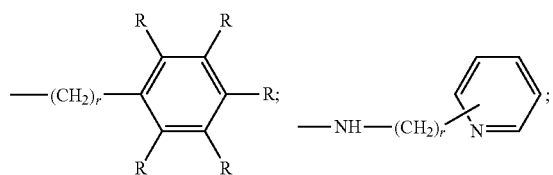

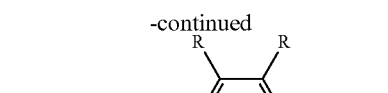

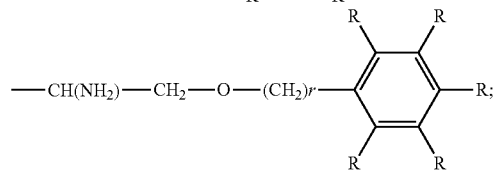

and optionally a combination thereof
wherein r is an integer from 0 to 2, R is independently selected from the group consisting of H, OH, OCH₃, NH₂, O(CH₂CH₂O)ₘH, and O(CH₂CH₂O)ₘCH₃ with m being an integer between 1 and 500;
wherein the polyethylenimine has from 10 to 2000 ethylenimine units.

2. The polyethylenimine of claim 1, wherein the polyethylenimine is branched.

3. The polyethylenimine of claim 1, wherein the polyethylenimine has a molecular weight of between 500 Da to 200,000 Da.

4. The polyethylenimine of claim 1, wherein the amine functions are modified or substituted by a radical X at a ratio of p from 0.1 to 0.9, or a ratio of p from 0.15 to 0.5, or a ratio of p from 0.2 to 0.4, or a ratio of p of about 0.30.

5. The polyethylenimine of claim 1, wherein R is independently selected from the group consisting of H, OH, OCH$_3$, and NH$_2$.

6. The polyethylenimine of claim 1, wherein r is 0 or 1.

7. The polyethylenimine of claim 1, wherein X is selected from the group consisting of

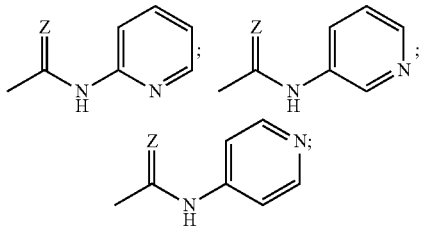

and optionally a combination thereof.

8. The polyethylenimine of claim 7, wherein Z is S.

9. The polyethylenimine of claim 8, wherein X is

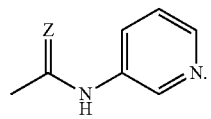

10. The polyethylenimine of claim 1, wherein X is selected from the group consisting of:

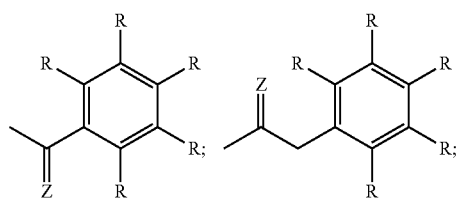

and optionally a combination thereof.

11. The polyethylenimine of claim 10, wherein X is

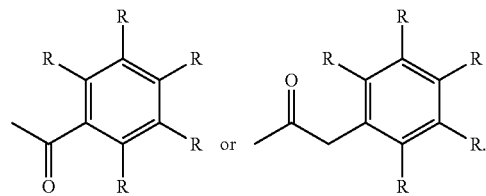

12. The polyethylenimine of claim 1, wherein at least 3 or 4 of the 5 R are H and the other R is selected from the group consisting of H, OH, NH$_2$, and OCH$_3$.

13. The polyethylenimine of claim 10, wherein at least 3 or 4 of the 5 R are H and the other R is selected from the group consisting of H, OH, NH$_2$, and OCH$_3$.

14. The polyethylenimine of claim 11, wherein at least 3 or 4 of the 5 R are H and the other R is selected from the group consisting of H, OH, NH$_2$, and OCH$_3$.

15. The polyethylenimine of claim 1, wherein X is selected from the group consisting of

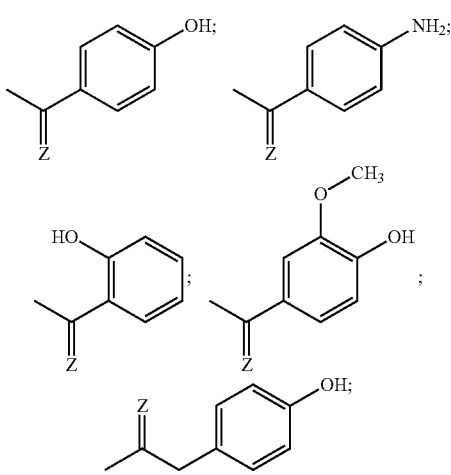

and optionally a combination thereof.

16. The polyethylenimine of claim 15, wherein Z is O.

17. The polyethylenimine of claim 1, wherein R1 is

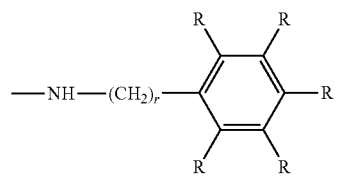

with 4 of the R being H and the other R being NH2, optionally in a para position and Z is S or O.

18. The polyethylenimine of claim 17, wherein Z is S and r is 0.

19. The polyethylenimine of claim 1, wherein X is C(=Z)—R$_1$ and R$_1$ is

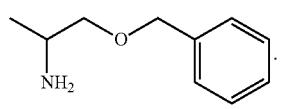

20. The polyethylenimine of claim 19, wherein Z is O.

21. The polyethylenimine of claim 1, wherein X is selected from the group consisting of

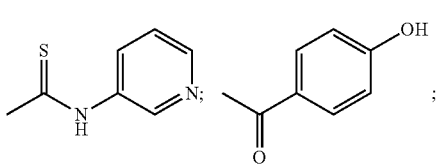

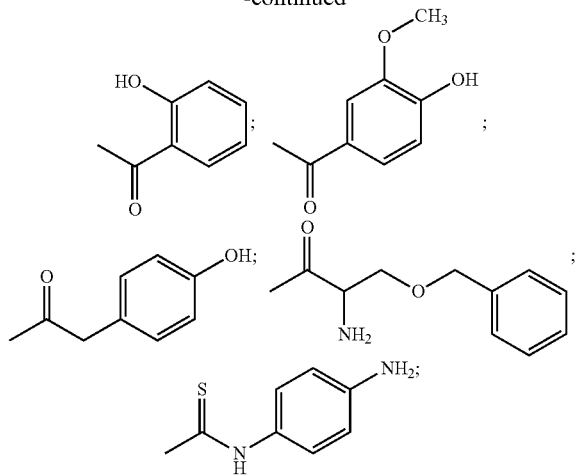

and optionally a combination thereof.

22. A composition comprising a polyethylenimine according to claim 1 and a molecule of interest non-covalently associated with the polyethylenimine, the molecule of interest being selected from the group consisting of nucleic acid, protein, peptide, chemical compound and drug.

23. The composition of claim 22, wherein the nucleic acid is selected from the group consisting of interfering RNA, antisense nucleic acid and ribozyme.

24. The composition of claim 22, wherein the nucleic acid is selected from the group consisting of small interfering RNA (siRNA), double-stranded RNA (dsRNA), double-stranded DNA (dsDNA), single-stranded RNA (ssRNA), single-stranded DNA (ssDNA), micro-RNA (miRNA), short hairpin RNA (shRNA), short hairpin DNA (shDNA) and DNA-RNA duplex.

25. An in vitro or ex vivo method for delivering a molecule of interest to a cell, said method comprising contacting the composition according to claim 22 with said cell.

26. A method for preparing a pharmaceutical composition for delivering a therapeutically active molecule to a mammal, said method comprising mixing the polyethylenimine according to claim 1 with the therapeutically active molecule.

* * * * *

UNITED STATES PATENT AND TRADEMARK OFFICE
CERTIFICATE OF CORRECTION

PATENT NO. : 8,945,927 B2
APPLICATION NO. : 13/637412
DATED : February 3, 2015
INVENTOR(S) : Guy Zuber et al.

Page 1 of 1

It is certified that error appears in the above-identified patent and that said Letters Patent is hereby corrected as shown below:

In the specification

Column 1,
Line 55, "therosclerosis" should read --atherosclerosis--.

Column 3,
Line 9, "S or 0;" should read --S or O;--.

Column 8,
Line 21, "nPEI" should read --πPEI--.

Column 30,
Line 66, "λX$_{max}$(ε" should read --λ$_{max}$(ε--.

Column 33,
Line 34, "during is" should read --during 1s--.

Column 37,
Line 41, "μ-globin" should read --β-globin--.

Column 42,
Line 46, "during is" should read --during 1s--.

Column 46,
Line 19, Table 3, "0.24 mVI" should read --0.24 mM--.

Signed and Sealed this
Fifteenth Day of December, 2015

Michelle K. Lee
*Director of the United States Patent and Trademark Office*

SEQUENCE LISTING

```
<160> NUMBER OF SEQ ID NOS: 5

<210> SEQ ID NO 1
<211> LENGTH: 19
<212> TYPE: RNA
<213> ORGANISM: Artificial
<220> FEATURE:
<223> OTHER INFORMATION: Sense strand of RNA duplex silencing luciferase
      gene

<400> SEQUENCE: 1
```

```
cuuacgcuga guacuucga                19

<210> SEQ ID NO 2
<211> LENGTH: 19
<212> TYPE: RNA
<213> ORGANISM: Artificial
<220> FEATURE:
<223> OTHER INFORMATION: Sense strand of untargeted pGL2luc RNA duplex

<400> SEQUENCE: 2
cguacgcgga auacuucga                19

<210> SEQ ID NO 3
<211> LENGTH: 18
<212> TYPE: RNA
<213> ORGANISM: Artificial
<220> FEATURE:
<223> OTHER INFORMATION: Sense strand of RNA duplex active for splicing
      interference

<400> SEQUENCE: 3
ccucuuaccu caguuaca                 18

<210> SEQ ID NO 4
<211> LENGTH: 20
<212> TYPE: RNA
<213> ORGANISM: Artificial
<220> FEATURE:
<223> OTHER INFORMATION: Sense strand of the control RNA duplex

<400> SEQUENCE: 4
ggccaaaccu cggcuuaccu               20

<210> SEQ ID NO 5
<211> LENGTH: 19
<212> TYPE: RNA
<213> ORGANISM: Artificial
<220> FEATURE:
<223> OTHER INFORMATION: Sense strand of the RNA duplex silencing the
      egfpluc fusion gene

<400> SEQUENCE: 5
cuuacgcuga guacuucga                19
```